US009580553B2

(12) United States Patent
Boydston et al.

(10) Patent No.: US 9,580,553 B2
(45) Date of Patent: Feb. 28, 2017

(54) THERMALLY-ACTIVATED SELF-IMMOLATIVE MATERIALS

(71) Applicants: University of Washington through its Center for Commercialization, Seattle, WA (US); Pacific Lutheran University, Tacoma, WA (US)

(72) Inventors: Andrew J. Boydston, Seattle, WA (US); Neal A. Yakelis, Tacoma, WA (US); Ronald Jay Berenson, Seattle, WA (US); Derek C. Church, Seattle, WA (US); Gregory I. Peterson, Seattle, WA (US); Michael Larsen, Seattle, WA (US)

(73) Assignees: University of Washington through its Center for Commercialization, Seattle, WA (US); Pacific Lutheran University, Tacoma, WA (US)

( * ) Notice: Subject to any disclaimer, the term of this patent is extended or adjusted under 35 U.S.C. 154(b) by 0 days.

(21) Appl. No.: 14/650,221

(22) PCT Filed: Dec. 9, 2013

(86) PCT No.: PCT/US2013/073928
§ 371 (c)(1),
(2) Date: Jun. 5, 2015

(87) PCT Pub. No.: WO2014/133620
PCT Pub. Date: Sep. 4, 2014

(65) Prior Publication Data
US 2015/0368403 A1    Dec. 24, 2015

Related U.S. Application Data

(60) Provisional application No. 61/734,448, filed on Dec. 7, 2012.

(51) Int. Cl.
| | | |
|---|---|---|
| *C08G 71/04* | (2006.01) |
| *A61K 47/48* | (2006.01) |
| *C08G 81/02* | (2006.01) |
| *C08G 85/00* | (2006.01) |
| *B82Y 5/00* | (2011.01) |

(52) U.S. Cl.
CPC ........ *C08G 71/04* (2013.01); *A61K 47/48053* (2013.01); *A61K 47/48192* (2013.01); *A61K 47/48246* (2013.01); *A61K 47/48715* (2013.01); *C08G 81/028* (2013.01); *C08G 85/002* (2013.01); *B82Y 5/00* (2013.01)

(58) Field of Classification Search
CPC ............... B82Y 5/00; A61K 47/48246; A61K 47/48023; A61K 47/48715; C08G 81/028; C08G 85/002
See application file for complete search history.

(56) References Cited

U.S. PATENT DOCUMENTS

| | | | |
|---|---|---|---|
| 4,506,473 A | 3/1985 | Waters, Jr. | |
| 2003/0096743 A1 | 5/2003 | Senter | |
| 2005/0176922 A1* | 8/2005 | McManus | ........ A61K 47/48215 528/310 |
| 2005/0256030 A1* | 11/2005 | Feng | ................ A61K 47/48338 530/329 |
| 2005/0271615 A1 | 12/2005 | Shabat et al. | |
| 2006/0051315 A1 | 3/2006 | Scaria et al. | |
| 2006/0269480 A1 | 11/2006 | Amir et al. | |
| 2012/0142711 A1 | 6/2012 | Warnecke | |
| 2012/0259267 A1 | 10/2012 | Almutairi et al. | |
| 2012/0270937 A1 | 10/2012 | Warnecke | |
| 2013/0017166 A1 | 1/2013 | Kabanov et al. | |
| 2014/0334991 A1 | 11/2014 | Johnson et al. | |
| 2016/0066553 A1 | 3/2016 | Boydston et al. | |

FOREIGN PATENT DOCUMENTS

| | | |
|---|---|---|
| WO | 2008/053479 A1 | 5/2008 |
| WO | 2011/038117 A2 | 3/2011 |
| WO | 2012/156918 A1 | 11/2012 |
| WO | 2013/020005 A2 | 2/2013 |

OTHER PUBLICATIONS

Esser-Kahn, A.P., et al., "Programmable Microcapsules From Self-Imnnolative Polymers," Journal of American Chemical Society 132(30):10266-10268, Aug. 2010.
Alkilany, A. M., et al., "Gold Nanorods: Their Potential for Photothermal Therapeutics and Drug Delivery, Tempered the Complexity of Their Biological Interactions," Advanced Drug Delivery Reviews 64:190-199, 2012.
Amir, R. J., et al., "Receiver-Amplifier, Self-Immolative Dendritic Device," Chemistry: A European Journal 13:812-821, 2007.
Avital-Shmilovici, M., and D. Shabat, "Self-Immolative Dendrimers: A Distinctive Approach to Molecular Amplification," Soft Matter 6:1073-1080, 2010.
Basudhar, D., et al., "Synthesis and Chemical and Biological Comparison of Nitroxyl- and Nitric Oxide-Releasing Diazeniumdiolate-Based Aspirin Derivatives," Journal of Medicinal Chemistry 56:7804-7820, Sep. 2013.

(Continued)

*Primary Examiner* — Gregory Listvoyb
(74) *Attorney, Agent, or Firm* — Christensen O'Connor Johnson Kindness PLLC; Juan Zheng; George Renzoni

(57) ABSTRACT

A polymer including a self-immolative polymer segment and a thermally-activated trigger moiety is described. The self-immolative polymer segment includes a head end, a tail end, and a plurality of repeating units. The trigger moiety includes a cycloaddition adduct that is covalently coupled to the head end of the self-immolative polymer segment. When the polymer is exposed to an activation temperature, the cycloaddition adduct undergoes retro-cycloaddition to release the self-immolative polymer segment. The self-immolative polymer segment then decomposes to sequentially release repeating units in a head-to-tail direction.

25 Claims, 4 Drawing Sheets

(56) References Cited

OTHER PUBLICATIONS

Blencowe, C. A., et al., "Self-Immolative Linkers in Polymeric Delivery Systems," Polymer Chemistry 2:773-790,2011.
Breschi, M. C., et al., "New NO-Releasing Pharmacodynamic Hybrids of Losartan and Its Active Metabolite: Design, Synthesis, and Biopharmacological Properties," Journal of Medicinal Chemistry 49(8):2628-2639, Jan. 2006.
Carter, J.M. et al., "Peptide-Based Hydrogen Sulphide-Releasing Gels," ChemComm 51:13131-13134, Jul. 2015.
Chaiyaveij, D., et al., "Copper(II)-Catalyzed Room Temperature Aerobic Oxidation of Hydroxamic Acids and Hydrazides to Acyl-Nitroso and Azo Intermediates, and Their Diels-Alder Trapping," Organic Letters 13(13):3442-3445, May 2011.
Cheng, L., et al., "PEGylated Micelle Nanoparticles Encapsulating a Non-Fluorescent Near-Infrared Organic Dye as a Safe and Highly-Effective Photothermal Agent for In Vivo Cancer Therapy," Advanced Functional Materials 23:5893-5902,2013.
Christie, C.C., et al. "C-Nitrosoformamides, a New Class of Transient Dienophiles Formed by Oxidation of N-Hydroxyureas," Journal of the Chemical Society Perkin Transactions 1:2469-2473, Mar. 1985.
Coulembier, O., et al., "Probe-Based Nanolithography: Self-Amplified Depolymerization Media for Dry Lithography," Macromolecules 43:572-574,2010.
Darensbourg, D.J., et al., "An Efficient Method of Depolymerization of Poly(cyclopentene carbonate) to Its Comonomers: Cyclopentene Oxide and Carbon Dioxide," Macromolecules 46:5850-5855,2013.
De Gracia Lux, C., et al., "Single UV or Near IR Triggering Event Leads to Polymer Degradation into Smaller Molecules," ACS Macro Letters 1:922-926, 2012.
Dewit, M.A., et al., "A Reduction Sensitive Cascade Biodegradable Linear Polymer," Journal of Polymer Science Part A: Polymer Chemistry 48:3977-3985, 2010.
Dewit, M.A. and E.R. Gillies, "A Cascade Biodegradable Polymer Based on Alternating Cyclization and Elimination Reactions," The Journal of the American Chemical Society 131:18327-18334, Jun. 2009.
Diéguez, M. and O. Pàmies, "Modular Phosphite-Oxazoline/Oxazine Ligand Library for Asymmetric Pd-Catalyzed Allyic Substitution Reactions: Scope and Limitations—Origin of Enantioselectivity," Chemistry: A European Journal 14:3653-3669,2008.
Frazier, C.P., et al., "Copper-Catalyzed Aerobic Oxidation of N-Substituted Hydroxylamines: Efficient and Practical Access to Nitroso Compounds," Organic Letters 14(14):3620-3623, May 2012.
Fukuto, J.M., et al., "The Physiological Chemistry and Biological Activity of Nitroxyl (HNO): The Neglected, Misunderstood, and Enigmatic Nitrogen Oxide," Chemical Research in Toxicology 18(5):790-801,2005.
Gao, Y., et al., "Controlled and Triggered Small Molecule Release from a Confined Polymer Film," ACS Applied Materials and Interfaces 5:9803-9808, Sep. 2013.
Ge, Y. and R.L. Moss, "Nitroxyl, Redox Switches, Cardiac Myofilaments, and Heart Failure: A Prequel to Novel Therapeutics?" Circulation Research 111:954-956, 2012.
Gillies, M.T., "The Role of Carbon Dioxide in Host-Finding by Mosquitoes (Diptera: Culicidae): A Review," Bulletin of Entomological Research 70:525-532, 1980.
Grüll, H. and S. Langereis, "Hyperthermia-Triggered Drug Delivery From Temperature-Sensitive Liposomes Using MRI-Guided High Intensity Focused Ultrasound," Journal of Controlled Release 161:317-327, Apr. 2012.
Guha, S., et al., "Clean Photothermal Heating and Controlled Release From Near-Infrared Dye Doped Nanoparticles Without Oxygen Photosensitization," Langmuir 31:7826-7834, Jul. 2015.
Huang, Z., et al., "Ethanesulfohydroxamic Acid Ester Prodrugs of Nonsteroidal Anti-Inflammatory Drugs (NSAIDs): Synthesis, Nitric Oxide and Nitroxyl Release, Cyclooxygenase Inhibition, Anti-Inflammatory, and Ulcerogenicity Index Studies," Journal of Medicinal Chemistry 54:1356-1364, Jan. 2011.
International Search Report and Written Opinion mailed Sep. 25, 2014 in corresponding International Application No. PCT/US2013/073928, filed Dec. 9, 2013, 9 pages.
Irvine, J.C., et al., "Nitroxyl (HNO): The Cinderella of the Nitric Oxide Story," Trends in Pharmacological Sciences 29(12):601-608,2008.
Kirby, G.W. and J.G. Sweeny, "Formation and Dienophilic Reactions of Transient C-Nitrosocarbonyl Compounds," Journal of Chemical Society Perkin Transactions 1:3250-3254, 1981.
Kirby, G.W., et al., "Formation and Reactions of C-Nitrosoformate Esters, a New Class of Transient Dienophiles," Journal of Chemical Society Perkin Transactions 1:1437-1442, 1985.
Knoll, A.W., et al., "Probe-Based 3-D Nanolithography Using Self-Amplified Depolymerization Polymers," Advanced Materials 22:3361-3365, 2010.
Köstler, S., et al., "Amphiphilic Block Coploymers Containing Thermally Degradable Poly(phthalaldehyde) Blocks," Journal of Polymer Science: Part A: Polymer Chemistry 47:1499-1509, 2009.
Kumar C.S.S.R. and F. Mohammad, "Magnetic Nanomaterials for Hyperthermia-Based Therapy and Controlled Drug Delivery," Advanced Drug Delivery Reviews 63:789-808, 2011.
Kwart, H. and K. King, "The Reverse Diels-Alder or Retrodiene Reaction," Chemical Review 68(4):415-447, 1968.
Li, M., et al., "Near-Infrared Light-Absorptive Stealth Liposomes for Localized Photothermal Ablation of Tumors combined with Chemotherapy," Advanced Functional Materials 25:5602-5610, 2015.
Matsuo, K., et al., "Alternative Photoinduced Release of HNO or NO From an Acyl Nitroso Compound, Depending on Environmental Polarity," ChemComm 46:3788-3790, May 2010.
Matsuo, K., et al., "Photoinduced Upregulation of Calcitonin Gene-Related Peptide in A549 Cells Through HNO Release From a Hydrophilic Photocontrollable HNO Donor," Chemical and Pharmaceutical Bulletin 60(8):1055-1062, May 2012.
Miao, Z., et al., "A Selective Phosphine-Based Fluorescent Probe for Nitroxyl in Living Cells," Bioorganic & Medicinal Chemistry Letters 25:16-19, 2015.
Norris, A.J., et al., "Nitroxyl Inhibits Breast Tumor Growth and Angiogenesis," International Journal of Cancer 122:1905-1910, 2008.
Nuñez, S.A., et al., "A Structurally Simple Self-Immolative Reagent That Provides Three Distinct, Simultaneous Responses per Detection Event," Journal of Organic Chemistry 76:10099-10113, Nov. 2011.
Paolocci, N., et al., "The Pharmacology of Nitroxyl (HNO) and Its Thearapeutic Potential: Not Just the Janus Face of NO1," Pharmacology & Therapeutics 113:442-458, 2007.
Peterson, G.I., et al., "1,2-Oxazine Linker as a Thermal Trigger for Self-Immolative Polymers," Polymer 55:5980-5985, 2014.
Peterson, G.I., et al., "Controlled Depolymerization: Stimuli-Responsive Self-Immolative Polymers," Macromolecules 45:7317-7328, Aug. 2012.
Redy, O., et al., "A Simple FRET-Based Modular Design for Diagnostic Probes," Organic & Biomolecular Chemistry 10:710-715, 2012.
Reutenauer, P., et al., "Room Temperature Dynamic Polymers Based on Diels-Alder Chemistry," Chemistry: A European Journal 15:1893-1900, 2009.
Roy, N. and J-M. Lehn, "Dynamic Covalent Chemistry: A Facile Room-Temperature, Reversible, Diels-Alder Reaction Between Anthracene Derivatives and N-Phenyltriazolinedione," Chemistry: An Asian Journal 6:2419-2425, 2011.
Sagi, A., et al., "Self-Immolative Polymers," The Journal of the American Chemical Society 130:5434-5435, 2009.
Seo, W. and S.T. Phillips, "Patterned Plastics That Change Physical Structure in Response to Applied Chemical . Signals," Journal of the American Chemical Society 132:9234-9235, 2010.
Shao, P., et al., "The Application of Thermosensitive Nanocarriers in Controlled Drug Delivery," Journal of Nanomaterials 2011:1-13, Mar. 2011.

(56) References Cited

OTHER PUBLICATIONS

Sindhu, T.J., et al., "Biological Activities of Oxazine and Its Derivatives: A Review," International Journal of Pharmacological Sciences and Research 4(11):134-143, Nov. 2013.

Strong, L.E., et al., "Hydrogel-Nanoparticle Composites for Optically Modulated Cancer Therapeutic Delivery," Journal of Controlled Release 178:63-68, 2014.

Switzer, C.H., et al., "The Emergence of Nitroxyl (HNO) as a Pharmacological Agent," Biochimica et Biophysica Acta 1787:835-840, 2009.

Ter Haar, G., and C. Coussios, "High Intensity Focused Ultrasound: Physical Principles and Devices," International Journal of Hyperthermia 23(2):89-104, Mar. 2007.

Wan, H., et al., "Facile Fabrication of a Near-Infrared Responsive Nanocarrier for Spatiotemporally Controlled Chemo-Photothermal Synergistic Cancer Therapy," Nanoscale 6:8743-8753, 2014.

Wang, W., and C. Alexander, "Self-Immolative Polymers," Angewandte Chemie International Edition 47:7804-7806, 2008.

Weinstain, R., et al., "Self-Immolative Comb-Polymers: Multiple-Release of Side-Reporters by a Single Stimulus Event," Chemistry: A European Journal 14:6857-6861, 2008.

Williams, K.A., et al., "Main-Chain Organometallic Polymers: Synthetic Strategies, Applications, and Perspectives," Chemical Society Reviews 36:729-744, 2007.

Wong, A.D., et al., "Amplified Release Through the Stimulus Triggered Degradation of Self-Immolative Oligomers, Dendrimers, and Linear Polymers," Advanced Drug Delivery Reviews 64:1031-1045, 2012.

Xu, Y., et al., "Production of Nitroxyl (HNO) at Biologically Relevant Temperatures From the Retro-Diels-Alder Reaction of N-Hydroxyurea-Derived Acyl Nitroso-9,10-Dimethylanthracene Cycloadducts,"Tetrahedron Letters 41:4265-4269, 2000.

Zeng, B., et al., "Nitroxyl (HNO) Release From New Functionalized N-Hydroxyurea-Derived Acyl Nitroso-9,10-dimethylanthracene Cycloadducts," Bioorganic & Medicinal Chemistry Letters 14:5565-5568, 2004.

Zhang, H., et al., "Self-Powered Microscale Pumps Based on Analyte-Initiated Depolymerization Reactions," Angewandte Chemie International Edition 51:2400-2404, 2012.

* cited by examiner

THERMALLY-ACTIVATED SELF-IMMOLATIVE MATERIALS

CROSS-REFERENCE TO RELATED APPLICATION

This application claims the benefit of U.S. Provisional Application No. 61/734,448, filed Dec. 7, 2012.

STATEMENT OF GOVERNMENT LICENSE RIGHTS

This invention was made with U.S. Government support under W911NF-11-1-0289 awarded by the U.S. Army Research Office. The U.S. Government has certain rights in the invention.

FIELD OF THE INVENTION

The present disclosure is directed to self-immolating polymers including a temperature-sensitive trigger group.

BACKGROUND

Self-immolating polymers ("SIPs") are a relatively new class of stimuli-responsive polymers that can undergo controlled head-to-tail depolymerization with the cleavage of a triggering group. See, e.g., Peterson et al., Macromolecules 2012, 45:7317-7328; Wang et al., Angew. Chem. Int. Ed. 2008, 47:7804-7806; Avital-Shmilovici et al., Adv. Drug Deliv. Rev. 2011, doi:10.1016/j.addr.2011.09.012; Blencowe et al., Polym. Chem. 2011, 2:773-790. Different triggering groups have been developed that undergo enzyme, redox, nucleophile, acid/base, or photo-mediated reactions to release an electron rich species that can initiate a cascade of elimination reactions and ultimately deconstruct the macromolecule.

A desirable feature of SIP triggering groups is that they are stable to other forms of stimuli, ensuring that depolymerization occurs only under a specific set of conditions as necessary for its desired application. While thermally unstable polymers have been developed, they undergo degradation in a non-controlled manner via random chain thermolysis. See, e.g., Williams et al., Chem. Soc. Rev. 2007, 36:729-744. The thermal degradation of a poly(phthalaldehyde) above 150° C. is an example of a SIP undergoing thermally-induced depolymerization. See, e.g., Kostler et al., Polym. Chem. 2009, 47:1499; Coulembier et al., Macromolecules 2010, 43, 572-574; and Knoll et al., Adv. Mater. 2010, 22:3361-3365. However, random mid-chain cleavage occurs in the thermal degradation of these poly(phthalaldehyde)s, leading to multi-directional depolymerization as opposed to the site-controlled cleavage of a specific triggering group followed by head-to-tail depolymerization.

Heat has not been previously described as a practical stimulus for SIP triggers. A site-controlled cleavage of a specific heat-sensitive triggering group followed by head-to-tail depolymerization can ensure the polymer is fully degraded to monomers, allows for tunable triggering temperatures, and can maintain the option of side chain release (not yet achieved with poly(phthalaldehyde)). By developing a heat-sensitive thermal trigger, the utility of SIPs can be improved.

SUMMARY

This disclosure relates, inter alia, to polymers including a self-immolative polymer segment and a thermally-activated trigger moiety. When the polymer is exposed to an activation temperature, the trigger moiety can decompose to release the self-immolative polymer segment. The self-immolative polymer segment then decomposes in a controlled manner in a head-to-tail direction.

In one aspect, this disclosure features a polymer including a self-immolative polymer segment including a head end, a tail end, and a plurality of repeating units; a trigger moiety including a cycloaddition adduct, wherein the cycloaddition adduct is covalently coupled to the head end of the self-immolative polymer segment.

In another aspect, this disclosure features a method for releasing one or more repeating units from the polymer above, including subjecting the polymer to a temperature sufficient to trigger retro-cycloaddition of the cycloaddition adduct to release the self-immolative polymer segment, wherein the self-immolative polymer segment then decomposes to sequentially release repeating units in a head-to-tail direction.

In yet another aspect, this disclosure features a method for delivering a therapeutic agent to a subject, including administering an effective amount of a polymer of claim 11 to a subject in need thereof.

In yet another aspect, this disclosure features a method for making a patterned structure, including applying a polymer of claim 1 to a substrate; and heating the substrate at predetermined locations to a temperature sufficient to effect depolymerization of the polymer to provide a patterned structure.

Aspects and/or embodiments of the methods can have one or more of the following features.

In some embodiments, the trigger moiety is configured to undergo a retro-cycloaddition reaction at a triggering temperature to cause the self-immolative polymer segment to decompose by releasing repeating units in a sequential head-to-tail direction. The triggering temperature can be from about 37° C. to about 120° C. (e.g., at about a physiological temperature). In some embodiments, the retro-cycloaddition reaction provides a diene and a carbamoylnitroso moiety.

In some embodiments, the cycloaddition adduct is a [4+2] cycloaddition adduct. The trigger moiety can include an adduct of a diene and a dienophile. The diene and/or the dienophile can be substituted.

In some embodiments, the diene is selected from anthracene, cyclopentadiene, 1,2,3,4,5-pentamethylcyclopentadiene, 1-hydroxymethyl-1,2,3,4,5-pentamethylcyclopentadiene, 1,3-cyclohexadiene, 1,3-butadiene, safranal, 1-hydroxymethyl-2,6,6-trimethyl-1,3-cyclohexadiene, cycloheptatriene, tropolone, butyltropolone, hinokitiol, butylhinokitiol, eucarvone, eucarveol, purpurogallin, trimethylpurpurogallin, 7-dehydrocholesterol, 3,5-cycloheptadienol, and substituted derivatives thereof.

The dienophile can include an alkene moiety (e.g., an electron-poor alkene moiety). In some embodiments, the dienophile is a maleimide moiety, acetylene moiety, a carbamoylnitroso moiety, an azo moiety, or substituted derivatives thereof.

Prior to incorporation into the self-immolative polymer segment, monomers used to form the self-immolating polymer can include an optionally substituted carbamate moiety, an optionally substituted carbonate moiety, an optionally substituted benzylic ether moiety, and an optionally substituted acetal moiety.

In some embodiments, the repeating unit is selected from:

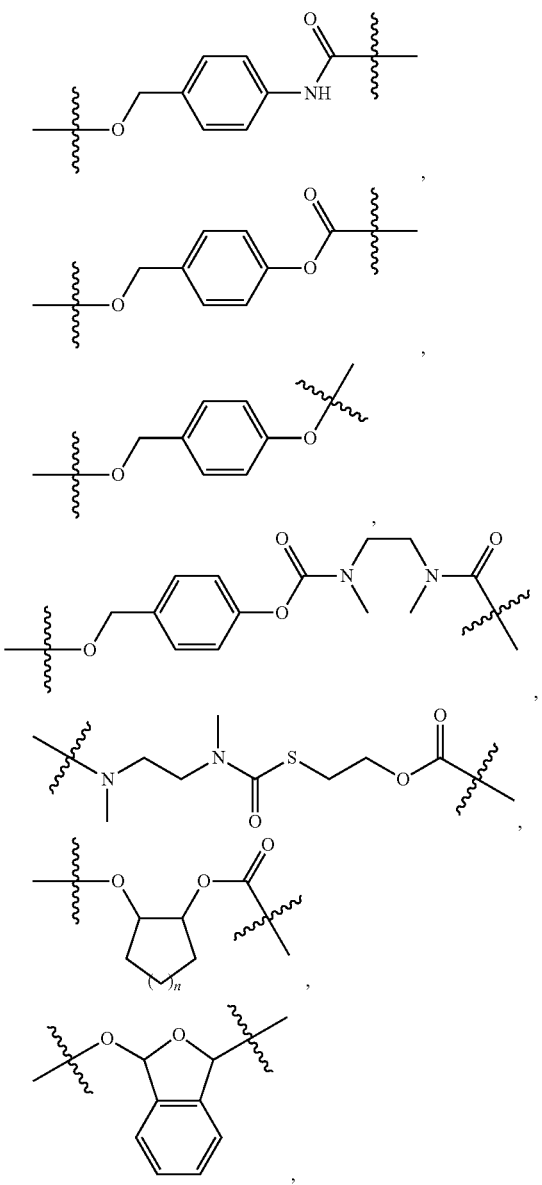

and
  substituted derivatives thereof.

The polymer can further include a covalently bound therapeutic agent. The therapeutic agent can be covalently bound to at least one of the repeating units. When the repeating unit to which the therapeutic agent is covalently bound to is released, the therapeutic agent can release simultaneously with or subsequent to the release of the repeating unit.

The polymer can include a water-soluble polymer segment covalently coupled to the self-immolative polymer segment, such that he polymer can be hydrophilic or water soluble. In some embodiments, the water-soluble polymer segment includes poly(ethylene glycol), poly(dimethylacrylamide), poly(vinylpyrrolidone), poly(vinyl alcohol), poly(N-(2-Hydroxypropyl) methacrylamide), poly(divinylether-maleic anhydride), poly(2-alkyl-2-oxazolines), xanthan gum, pectin, dextran, or any combination thereof.

In some embodiments, the method for making a patterned structure includes applying the polymer at the predetermined locations. In some embodiments, the method for making a patterned structure further includes applying one or more additional materials to the substrate before heating the substrate at the predetermined locations.

Other features and advantages of the disclosure will be apparent from the following detailed description, and from the claims.

DETAILED DESCRIPTION

A stimuli-responsive polymer that can be thermally activated to undergo a head-to-tail depolymerization is described. The polymer includes a self-immolative polymer segment and a trigger moiety. The self-immolative polymer segment includes a head end, a tail end, and repeating units. The trigger moiety is heat-sensitive and therefore can be thermally activated.

Figure 1:
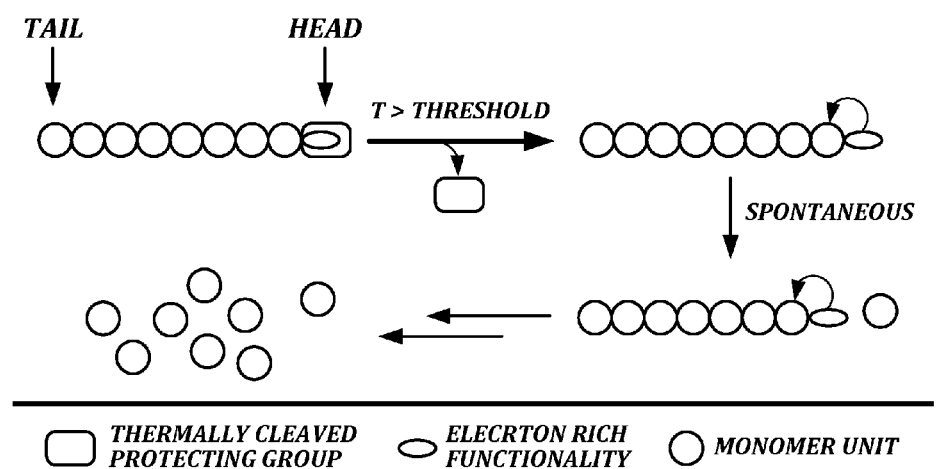
FIG. 1 is a schematic representation of the thermally-activated depolymerization of a self-immolative polymer.

Referring to FIG. 1, in some embodiments, the trigger moiety is covalently bound to a terminus (e.g., the head end) of the self-immolative polymer segment. Upon thermal activation of the trigger above a given threshold temperature, the self-immolative polymer segment begins a sequential release of the repeating units. Upon thermal activation, the trigger decomposes to reveal an electron-rich functionality that can initiate a release of a first repeating unit adjacent to the trigger moiety. Release of the first repeating unit unmasks a subsequent electron rich functionality on a second repeating unit adjacent to the first repeating unit, which then initiates the release of the second repeating unit while unmasking yet another electron rich functionality on a third repeating unit adjacent to the second repeating unit. The repeating unit release process (e.g., a depolymerization) continues thus in a sequential manner, resulting in a successive release of repeating units and the progressive shortening of the self-immolative polymer chain with each iteration, until all repeating units are released (FIG. 1). Release of the repeating groups can occur in a directional manner, such as in a head to tail direction. An example of a self-immolative polymer triggering and depolymerization is shown in Scheme 1.

Scheme 1

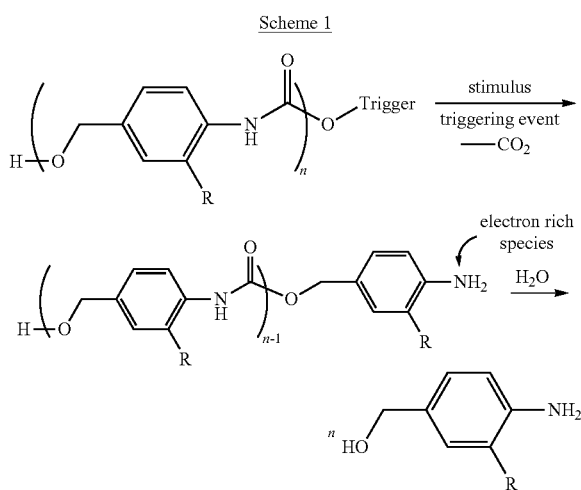

An electron-rich functionality can include lone pair electrons that can participate in nucleophilic attack or elimination (e.g., conjugated elimination) reactions. For example, the electron-rich functionality can include an amine (e.g., an unsubstituted amine, an alkylamine, a dialkylamine), a hydroxyl, a phenoxide or other alkoxide, a thiol, and/or a carboxylate group. The nucleophilic attack can occur intramolecularly, for example, within the self-immolative polymer segment itself to release repeating units by formation of a cyclic group (e.g., a cyclic urea).

DEFINITIONS

At various places in the present specification, substituents of compounds of the disclosure are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the disclosure, which are, for clarity, described in the context of separate embodiments, can also be provided in combination in a single embodiment.

Conversely, various features of the disclosure which are, for brevity, described in the context of a single embodiment, can also be provided separately or in any suitable subcombination.

The term "n-membered" where n is an integer typically describes the number of ring-forming atoms in a moiety where the number of ring-forming atoms is n. For example, piperidinyl is an example of a 6-membered heterocycloalkyl ring and 1,2,3,4-tetrahydro-naphthalene is an example of a 10-membered cycloalkyl group.

As used herein, the term "substituted" or "substitution" is meant to refer to the replacing of a hydrogen atom with a substituent other than H. For example, an "N-substituted piperidin-4-yl" refers to replacement of the H atom from the NH of the piperdinyl with a non-hydrogen substituent such as, for example, alkyl.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 10, from 1 to about 8, from 1 to about 6, from 1 to about 4, or from 1 to about 3 carbon atoms.

As used herein, "alkenyl" refers to an alkyl group having one or more double carbon-carbon bonds. Example alkenyl groups include ethenyl, propenyl, and the like. The term "alkenylenyl" refers to a divalent linking alkenyl group.

As used herein, "alkynyl" refers to an alkyl group having one or more triple carbon-carbon bonds. Example alkynyl groups include ethynyl, propynyl, and the like. The term "alkynylenyl" refers to a divalent linking alkynyl group.

As used herein, "haloalkyl" refers to an alkyl group having one or more halogen substituents. Example haloalkyl groups include $CF_3$, $C_2F_5$, $CHF_2$, $CCl_3$, $CHCl_2$, $C_2Cl_5$, and the like.

As used herein, "alkoxy" refers to an —O-alkyl group. Example alkoxy groups include methoxy, ethoxy, propoxy (e.g., n-propoxy and isopropoxy), t-butoxy, and the like.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic cyclic hydrocarbons including cyclized alkyl, alkenyl, and alkynyl groups. Cycloalkyl groups can include mono- or polycyclic (e.g., having 2, 3 or 4 fused rings) ring systems as well as spiro ring systems. Ring-forming carbon atoms of a cycloalkyl group can be optionally substituted by oxo or sulfido. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like. Also included in the definition of cycloalkyl are moieties that have one or more aromatic rings fused (i.e., having a bond in common with) to the cycloalkyl ring, for example, benzo or thienyl derivatives of pentane, pentene, hexane, and the like.

As used herein, "heteroaryl" groups refer to an aromatic heterocycle having at least one heteroatom ring member such as sulfur, oxygen, or nitrogen. Heteroaryl groups include monocyclic and polycyclic (e.g., having 2, 3 or 4 fused rings) systems. Examples of heteroaryl groups include without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "heterocycloalkyl" refers to non-aromatic heterocycles including cyclized alkyl, alkenyl, and alkynyl groups where one or more of the ring-forming carbon atoms is replaced by a heteroatom such as an O, N, or S atom. Heterocycloalkyl groups can be mono- or polycyclic (e.g., having 2, 3, 4 or more fused rings or having a 2-ring, 3-ring, 4-ring spiro system (e.g., having 8 to 20 ring-forming atoms). Heterocycloalkyl groups include monocyclic and polycyclic groups. Example "heterocycloalkyl" groups include morpholino, thiomorpholino, piperazinyl, tetrahydrofuranyl, tetrahydrothienyl, 2,3-dihydrobenzofuryl, 1,3- benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Ring-forming carbon atoms and heteroatoms of a heterocycloalkyl group can be optionally substituted by oxo or sulfido. Also included in the definition of heterocycloalkyl are moieties that have one or more aromatic rings fused (i.e., having a bond in common with) to the nonaromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, "halo" or "halogen" includes fluoro, chloro, bromo, and iodo.

As used herein, "arylalkyl" refers to alkyl substituted by aryl and "cycloalkylalkyl" refers to alkyl substituted by cycloalkyl. An example arylalkyl group is benzyl.

As used herein, "amino" refers to $NH_2$.

As used herein, "alkylamino" refers to an amino group substituted by an alkyl group.

As used herein, "dialkylamino" refers to an amino group substituted by two alkyl groups that can be the same, or different from one another.

Unless otherwise defined, all technical and scientific terms used herein have the same meaning as commonly understood by one of ordinary skill in the art. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Specific elements of any foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

Trigger Moiety

The trigger moiety is heat-sensitive. As used herein, "heat-sensitive" refers to a moiety that is decomposed upon exposure to a certain temperature, such as a physiological temperature or a temperature above a physiological temperature. In some embodiments, the trigger moiety includes a cycloaddition adduct. The cycloaddition adduct can include a [4+2] cycloaddition adduct (e.g., a Diels-Alder adduct) of a diene and a dienophile.

Without wishing to be bound by theory, it is believed that the Diels-Alder (DA) reaction involves covalent coupling of a "diene" with a "dienophile" to provide a cyclohexene or heterocyclohexene cycloadduct. See, for example, Kwart, H., and K. King, Chem. Rev. 68:415, 1968. Most DA cycloadditions can be described by a symmetry-allowed concerted mechanism without generating the biradical or zwitterion intermediates. Among many features of the DA reaction is that the resultant adducts can be reversibly thermally cleaved to regenerate the starting materials (i.e., diene and dienophile).

As used herein, the term "diene" refers to a 1,3-diene that is reactive toward a dienophile to provide a [4+2] (Diels-Alder) cycloaddition product (i.e., a cyclohexene). Suitable diene moieties include any diene (i.e., 1,3-diene) moiety that is reactive in forming a [4+2] cycloaddition product with a dienophile. For example, the diene moiety can include, anthracene, cyclopentadiene, 1,2,3,4,5-pentamethylcyclopentadiene, 1-hydroxymethyl-1,2,3,4,5-pentamethylcyclopentadiene, 1,3-cyclohexadiene, 1,3-butadiene, safranal, 1-hydroxymethyl-2,6,6-trimethyl-1,3-cyclohexadiene, cycloheptatriene, tropolone, butyltropolone, hinokitiol, butylhinokitiol, eucarvone, eucarveol, purpurogallin, trimethylpurpurogallin, 7-dehydrocholesterol, and/or 3,5-cycloheptadienol, and substituted derivatives thereof. In some embodiments, the diene moiety is substituted with one or more (e.g., 1, 2, 3, 4, 5, or 6) substituent groups. The substituent group can include any group that does not interfere with the release of a given repeating unit or trigger moiety. For example, the substituent groups are each independently selected from halo, $C_{1-8}$ alkyl, $C_{1-8}$ haloalkyl, aryl, arylalkyl, $C_{1-8}$ alkoxy, heteroaryl, heteroarylalkyl, cycloalkyl, heterocycloalkyl, OH, C(O), and C(O)H, wherein said $C_{1-8}$ alkyl, $C_{1-8}$ haloalkyl, aryl, arylalkyl, $C_{1-8}$ alkoxy, heteroaryl, heteroarylalkyl, cycloalkyl or heterocycloalkyl groups is optionally substituted with OH. In some embodiments, the one or more substituent groups are each independently selected from halo, $C_{1-8}$ alkyl, aryl, $C_{1-8}$ alkoxy, cycloalkyl, OH, and C(O), wherein said $C_{1-8}$ alkyl, aryl, $C_{1-8}$ alkoxy, or cycloalkyl is optionally substituted with OH. For example, the substituent group can be butyltropolone, butylhinokitiol, trimethylpurpurogallin, purpurogallin tetramethyl ether, pentamethyl cyclopentadiene, hexamethyl cyclopentadiene, and the like.

In some embodiments, the diene is:

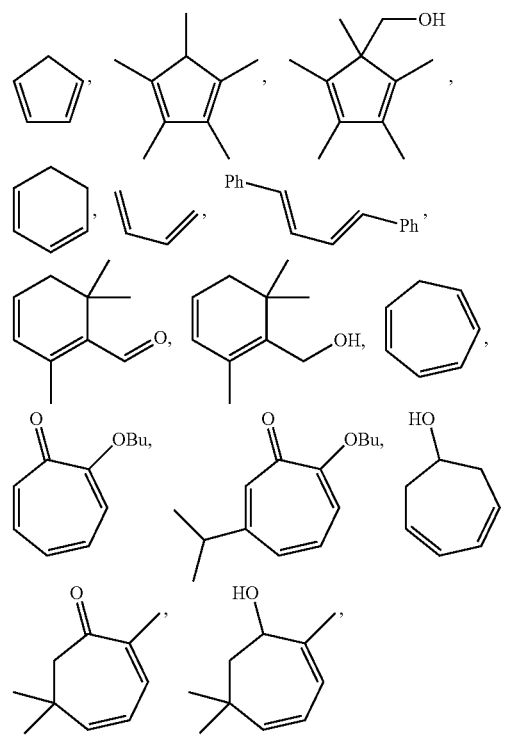

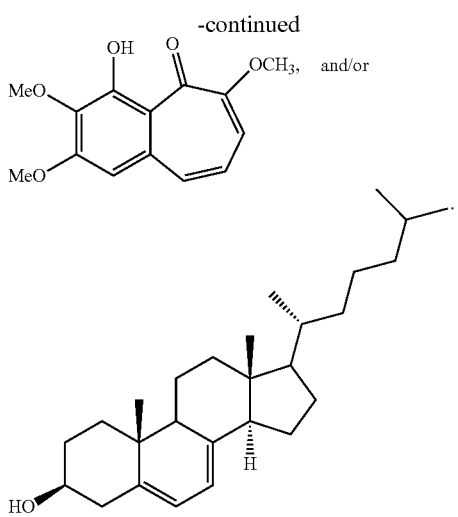

The diene moiety can be covalently coupled to the self-immolative polymer segment backbone by the reaction of a suitable functional group on the diene moiety (e.g., hydroxyl, amine, alkylamine, dialkylamine, thiol, group) with a suitable functional group on the polymer (e.g., a carbonate moiety, carbamate moiety, isocyanate moiety, alkyl halide, aldehyde moiety) to form carbonate, carbamate, ether, or acetal linkages.

The trigger moiety includes one or more dienophile or dienophile precursor moieties. The term "dienophile" refers to an alkene that is reactive toward a diene to provide a [4+2] cycloaddition product. The term "dienophile precursor" refers to a moiety that can be converted to a dienophile. Suitable dienophile moieties include any dienophile moiety that is reactive in forming a [4+2] cycloaddition product with a diene. Suitable dienophile precursor moieties include any dienophile precursor moiety that provides a dienophile that is reactive in forming a [4+2] cycloaddition product with a diene. The dienophile can include an alkene moiety (e.g., an electron-poor alkene moiety). In some embodiments, the dienophile moiety is selected from a maleimide, maleate esters, an acetylene dicarboxylate, carbamoylnitroso moiety, and an azo (e.g., R—N=N—R') moiety. In some embodiments, the dienophile moiety is substituted with one or more (e.g., 1, 2, 3, 4, 5, or 6) substituent groups. The substituent group can include any group that does not interfere with the release of a given repeating unit or trigger moiety. For example, the substituent groups are each independently selected from halo, $C_{1-8}$ alkyl, $C_{1-8}$ haloalkyl, aryl, arylalkyl, $C_{1-8}$ alkoxy, heteroaryl, heteroarylalkyl, cycloalkyl, heterocycloalkyl, OH, C(O), and C(O)H, wherein said $C_{1-8}$ alkyl, $C_{1-8}$ haloalkyl, aryl, arylalkyl, $C_{1-8}$ alkoxy, heteroaryl, heteroarylalkyl, cycloalkyl or heterocycloalkyl groups is optionally substituted with OH. In some embodiments, the substituent groups are each independently selected from halo, $C_{1-8}$ alkyl, $C_{1-8}$ alkyl, $C_{1-8}$ haloalkyl, aryl, arylalkyl, heteroaryl, heteroarylalkyl, cycloalkyl, and heterocycloalkyl groups. In some embodiments, the one or more substituent groups are each independently selected from halo, $C_{1-8}$ alkyl, or aryl.

The dieneophile moiety can be covalently coupled to the self-immolative polymer segment backbone by reaction of a suitable functional group on the dienophile or dienophile precursor (e.g., hydroxylamine) with a suitable functional group on the polymer (e.g. carbamate).

The trigger moiety's diene and dienophile can be selected for their reactivity profile to suit a particular application. Reactivity profile refers to the reaction conditions (e.g., temperature) required to associate the diene and dienophile to from a [4+2] cycloadduct (i.e., Diels Alder reaction) and to dissociate the [4+2] cycloadduct to form the diene and dienophile (i.e., retro-Diels-Alder reaction). The chemical nature of the diene and dienophile (e.g., substituents and substitution pattern) determine the reactivity profile.

In some embodiments, cycloaddition adducts between carbamoylnitroso-containing molecules and various dienes are used for temperature-sensitive trigger moieties that can unmask an electron rich species. Referring to Scheme 2, cycloreversion of the adduct releases the carbamoylnitroso group which is then hydrolytically degraded to an electron rich group (e.g., an amine, an alkylamine, a dialkylamine).

Scheme 2

The trigger moiety can be activated at various temperatures, depending on the cycloaddition adduct. For example, adducts formed with cyclopentadiene can be stable for up to 2 h at 80° C. before they undergo cycloreversion. Adducts formed with 9,10-dimethylanthracene (9,10-DMA) can undergo cycloreversion at room temperature (RT), and display half-lives at 40° C. ranging from 15-150 minutes. Examples 1 and 3 illustrate some embodiments of thermally-activated self-immolating polymers that include cyclopentadiene and anthracene-based adducts. The cycloreversion can occur in a temperature range that is useful for the polymer's desired application while minimizing premature trigger release (e.g., during storage or processing). In some embodiments, the trigger moiety activation temperature (triggering temperature) is about 30° C. or more (e.g., about 32° C. or more, about 37° C. or more, about 40° C. or more, about 50° C. or more, about 70° C. or more, about 100° C. or more) and/or about 120° C. or less (e.g., about 100° C. or less, about 70° C. or less, about 50° C. or less, about 40° C. or less, about 37° C. or less, or about 32° C. or less). In some embodiments, the triggering temperature is from about 35° C. to about 120° C. (e.g., from about 32° C. to about 40° C., from about 37° C. to about 120° C., from about 37° C. to about 40° C., or from about 37° C. to about 50° C.). For example, the triggering temperature can be about a physiological temperature (e.g., 37° C.).

Referring to Scheme 3, in some embodiments, aromatic heterocyclic compounds are used as the diene component of the cycloaddition adduct. The cycloaddition adduct can remain attached to the SIP.

Scheme 3

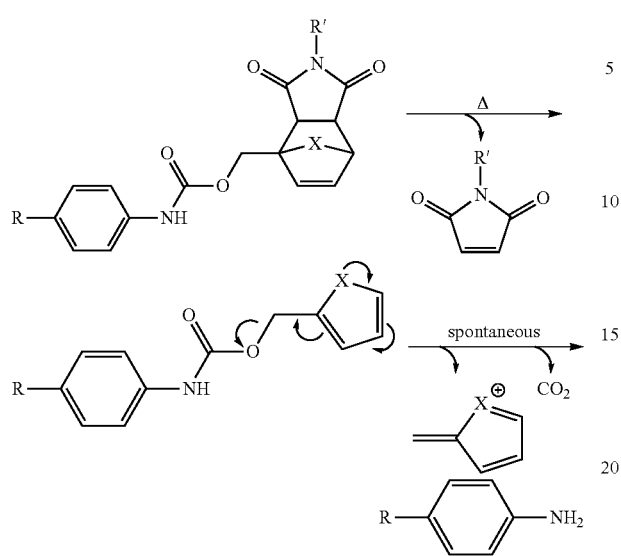

As shown in Scheme 3, the electron rich heteroatom X within the heterocycle is not in conjugation with the SIP backbone, when the SIP is connected to an intact trigger moiety. After thermal activation, the heterocyclic diene is released from the trigger moiety, and the electron rich heteroatom X is now in conjugation with the SIP backbone and able to release the electron rich amine. The kinetics of the heterocyclic elimination can be controlled by choosing heteroatoms and/or the heterocycle's pendant groups (e.g., R' in Scheme 3). The thermal activation barrier can be tuned by choice of heterocyclic aromatic ring and dienophile components. Dieneophiles such as maleimides, maleate esters, or acetylene dicarboxylates can modified into functionalized dienophiles.

Although representative trigger moieties are described above, it will be appreciated that the trigger moieties of the disclosure can include a variety of dienophiles and dienes.

Self-Immolative Polymer Segment

The self-immolative polymer can have two repeating units or more (e.g., 10 repeating units or more). Self-immolative polymer segments are described, for example, in Peterson et al., Controlled Depolymerization: Stimuli-Responsive Self-Immolative Polymers, Macromolecules 2012, 45, 7317-28. The self immolative polymer segment can be in the form of linear polymers or dendrimers, and adapted to facilitate release of small molecules pendant to the SIP main chain. The self-immolative polymer segment can include polyurethanes and/or polyethers. Examples of self-immolative polymers, their synthesis, and depolymerization mechanism are described, for example, in Peterson et al., Controlled Depolymerization: Stimuli-Responsive Self-Immolative Polymers, Macromolecules 2012, 45:7317-28; U.S. Patent Publication No. 2012/0259267; U.S. Patent Publication No. US2012/0270937; U.S. Patent Publication No. 2005/0271615; U.S. Patent Publication No. 2006/0269480; International Publication No. WO2011/038117; and International Publication No. WO2008/053479; the contents of each of which are herein incorporated in their entireties.

The self-immolative polymer segment includes optionally substituted repeating units. For example, prior to incorporation into the self-immolative polymer segment, the repeating unit can include a carbamate moiety, carbonate moiety, benzylic ether moiety, and/or acetal moiety. In some embodiments, the repeating unit is

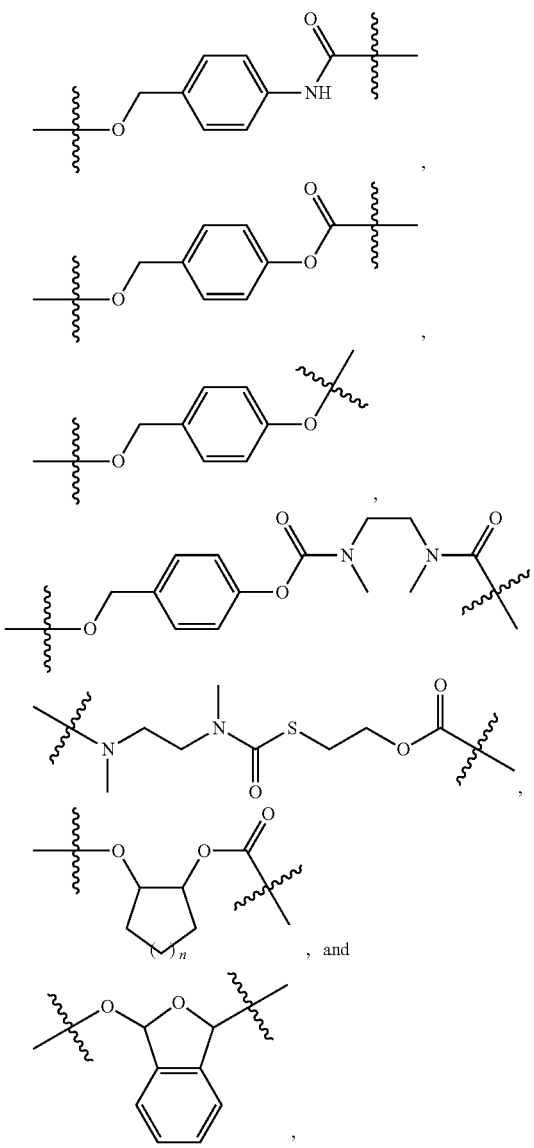

, and and substituted derivatives thereof, wherein n is 1, 2, 3, or 4. One or more repeating units can be optionally substituted with one or more (e.g., 1, 2, 3, 4, 5, or 6) substituent groups. The substituent group can include any group that does not interfere with the release of a given repeating unit or trigger moiety. For example, the substituent groups can be independently selected from halo, $C_{1-8}$ alkyl, $C_{1-8}$ haloalkyl, aryl, arylalkyl, $C_{1-8}$ alkoxy, heteroaryl, heteroarylalkyl, cycloalkyl, heterocycloalkyl, and OH, wherein said $C_{1-8}$ alkyl, $C_{1-8}$ haloalkyl, aryl, arylalkyl, $C_{1-8}$ alkoxy, heteroaryl, heteroarylalkyl, cycloalkyl or heterocycloalkyl groups is optionally substituted with OH. In some embodiments, the one or more substituent groups are each independently selected from halo, $C_{1-8}$ alkyl, or aryl. In some embodiments, the substituent is a covalently bound therapeutic agent, such that the therapeutic agent is a pendant side chain on a given repeating unit.

In some embodiments, a portion of the repeating units of the self-immolative polymer segment is substituted. The substituted portion can be 10 mol % or more (e.g., 20 mol % or more, 40 mol % or more, 60 mol % or more, or 80 mol % or more) and/or 90 mol % or less (e.g., 80 mol % or less, 60 mol % or less, 40 mol % or less, or 20 mol % or less). For example, about 10 mol % (e.g., about 20 mol %, 40 mol %, 60 mol %, or 80 mol %) of the repeating units in the self-immolative polymer can be substituted.

The self-immolative polymer can undergo depolymerization upon removal of the trigger moiety. Three distinct depolymerization mechanisms have been demonstrated: (1) 1,6- and 1,4-eliminations to form quinone methides, (2) cyclizations to form imidazolidinones, oxazolidinones, or 1,3-oxathiolan-2-ones, epoxides, or carbonates, and (3) breakdown of hemiacetals to dialdehyde monomers. See, e.g., Peterson et al., Controlled Depolymerization: Stimuli-Responsive Self-Immolative Polymers, Macromolecules 2012, 45:7317-28, herein incorporated in its entirety. Each mechanism exhibits distinct breakdown kinetics, and the times for each to reach complete depolymerization are qualitatively ranked as: hemiacetal eliminations<1,6-eliminations<1,4-eliminations<cyclization-eliminations. Some depolymerization pathways produce highly reactive monomeric intermediates whereas others result in more stable small molecule components.

As an example, repeating units containing p-benzylic or o-vinylogous linkages eliminate in a 1,6-fashion, whereas 1,4-eliminations are observed from repeat units bearing xox-benzylic connectivities. In each case, a reactive quinone methide intermediate is formed. The released species can either be a small molecule output or an activated chain end poised to continue the depolymerization. As another example, self-immolative depolymerization can be based upon an intramolecular 5-exo-trig cyclization with concurrent release of an electron rich leaving group, as shown in, e.g., DeWit et al., *J. Am. Chem. Soc.* 2009, 131:18327-18334; DeWit et al., *J. Polym. Sci., Part A: Polym. Chem.* 2010, 48:3977-3985; and de Gracia Lux, et al., *ACS Macro Lett.* 2012, doi:10.1021/mz3002403, each herein incorporated in its entirety. This has been demonstrated to occur in systems forming ureas, carbamates, and thiocarbonates. Cyclizing units can be utilized to tune the kinetics of the degradation process. As a further example, a head-to-tail self-immolative breakdown of poly(phthalaldehyde) can occur much more rapidly than depolymerization observed from other types of SIPs. Upon trigger cleavage at the head of the polymer, a hemiacetal is revealed. Subsequent reversion to the free aldehyde eliminates the next hemiacetal, thus propagating the self-immolative sequence. In solution, this process can take place in a matter of seconds, and depolymerization in solid materials can require 15 min for complete reversion to phthalaldehyde monomer units. See, e.g., Seo et al., *J. Am. Chem. Soc.* 2010, 132:9234-9235; Zheng et al., *Angew. Chem. Int. Ed.* 2012, 51:2400-2404, each herein incorporated in its entirety.

Water Solubility

In some embodiments, hydrophilic or water-soluble variants of thermally-activated SIPs are prepared by incorporating the SIP segments into block copolymers that include one or more water-soluble polymer segments. Examples 1 and 2 illustrate some embodiments of hydrophilic or water-soluble variants of thermally-activated SIPs. The SIP segments and the water-soluble polymer segments can be covalently coupled. A general synthetic procedure for covalently coupling water-soluble polymer segments to SIP segments is provided, for example, in Scheme 8, infra. In some embodiments, a SIP segment is covalently bound to one water-soluble polymer segment. In some embodiments, a SIP segment is covalently bound to a water-soluble segment at each SIP segment terminus.

The water soluble segments can include, for example, poly(dimethylacrylamide) (PDMA), poly(ethylene glycol) (PEG), poly(vinylpyrrolidone), poly(vinyl alcohol), poly(N-(2-Hydroxypropyl) methacrylamide), poly(divinylether-maleic anhydride), poly(2-alkyl-2-oxazolines), xanthan gum, pectin, dextran, or any combination thereof. The water-soluble polymer segments can be non-depolymerizing. For example, the repeating units of water-soluble polymer segments can be resistant to elimination reactions.

Polymer Applications

The thermally-activated depolymerization of the self-immolative polymer can lead to an amplified release of small molecules (e.g., reporter molecules, prodrugs, etc.) and/or a change in the physical properties of a solid state material including the polymer. For example, the self-immolative polymers can have applications in areas such as sensory materials, therapeutic agent delivery platforms, self-healing composites, biomaterials, and lithographic plastics. Applications for the self-immolative polymers are described, for example, in Peterson et al., Controlled Depolymerization: Stimuli-Responsive Self-Immolative Polymers, Macromolecules 2012, 45:7317-28; U.S. Patent Publication No. 2012/0259267; U.S. Patent Publication No. US2012/0270937; U.S. Patent Publication No. 2005/0271615; U.S. Patent Publication No. 2006/0269480; International Publication No. WO2011/038117; and International Publication No. WO2008/053479; the contents of each of which are herein incorporated in their entireties. The polymers can possess repeating units that can facilitate tuning of the polymeric properties according to the desired application or function. In some embodiments, the polymers are incorporated into materials that have non-depolymerizing components, such as multiblock copolymers and microcapsules.

Sensors

SIPs are well suited for applications as sensory materials due to their signal amplification ability as a given polymer is decomposed to numerous repeating units, which can decrease the detection limit for a particular analyte capable of trigger activation. Monitoring signal output can include observation of diagnostic UV-vis or photoluminescence signals from released repeating units, which can serve as reporting molecules. For example, release of p-nitrophenol can be detected and quantified via UV-vis spectrometry, and release of fluorogenic repeating units (e.g., 6-aminoquinoline) can be monitored via photoluminescence spectrometry, and generation of FRET pairs for fluorescent signal detection can be achieved. See, e.g., Sagi et al., *J. Am. Chem. Soc.* 2008, 130:5434-5435; Amir et al., *Chem. Eur. J.* 2007, 13:812-821, and Redy et al., *Org. Biomol. Chem.* 2012, 10:710-715, each herein incorporated by reference in its entirety.

Therapeutic Agent Delivery

In some embodiments, clinical areas that could benefit from the use of thermally-activated SIPs as therapeutic agent delivery vehicles include oncology, pain/addiction, and psychiatry. Without wishing to be bound by theory, it is believed that the biological and consequent therapeutic effects of many therapeutic agents are directly related to the amount of therapeutic agent to which the target tissue or organ is exposed. The therapeutic effects can be related to both the concentration of the therapeutic agent as well as the time of exposure. The combination of these two parameters can be calculated and is known as Area Under the Curve (AUC).

High concentrations of many therapeutic agents are associated with side effects and toxicities. Therefore, therapeutic agent doses must be reduced to be safe. This can compromise therapeutic efficacy. One way to overcome this problem is to prolong exposure time of the therapeutic agent to the target tissue. This can be done using a variety of approaches for large molecules such as proteins and polypeptides, such as hormones, but there are only limited approaches to do this with small molecule therapeutic agents. Most of these technologies are used to enable slow release of orally-administered therapeutic agents, which are incorporated into polymers that gradually degrade over time in the gastrointestinal tract and are then absorbed into the body.

Thermally-activated SIPs can solve a number of previously unaddressed problems when used as therapeutic agent delivery vehicles. For example, therapeutic agent-coupled thermally-activated SIPs, when administered to a subject, can expose the subject to approximately constant concentrations of therapeutic agent over time. This can be safer and more effective than bolus administration of therapeutic agents. Additionally, administration of the therapeutic agent-coupled thermally-activated SIPs can be a more convenient means of prolonged therapeutic agent release than the frequent dosing or continuous infusion using pumps that have previously been used to achieve consistent levels over the long periods of time. Furthermore, a thermally-activated depolymerization process can provide increased stability toward downstream chemical reactions such as those needed during therapeutic agent conjugation; consistent rate of activation from patient to patient, since physiological temperature exhibit little variance; and maximum entropy of activation in comparison with potential background reactions such as polymer hydrolysis.

Many therapeutic agents, including both small molecules and proteins, have short half-lives when they are administered to subjects. For this reason, the therapeutics may not provide sustained levels to be of therapeutic benefit to subjects. In other cases, the therapeutic agents must be delivered frequently, which is inconvenient for subjects. In still other cases, the therapeutic agents must be administered via continuous infusion over several days, which require a pump, also inconvenient for patients. For example, the cancer chemotherapy therapeutic agent, 5-fluoruracil, has a very short half-life, and it is often given by continuous infusion over days in the hospital or several days to weeks via an infusion pump in the outpatient setting. Alternatively, 5-fluoruracil can be coupled to thermally-activated SIPs and administered to a subject parenterally. Such infrequent and convenient administration can result in relatively constant levels of the therapeutic agent in the body of the patient.

Thus, as therapeutic agent delivery vehicles, SIPs can enable (1) high therapeutic agent loading, (2) release of multiple therapeutic agent molecules following a single initiation event, (3) covalent attachment of therapeutic agent molecules to the carrier, and (4) pseudo-zero order release kinetics. Parenterally (e.g., intravenously, subcutaneously, and intraperitoneally) administered thermally-activated SIPs of the present disclosure that are coupled to therapeutic agents (i.e., drugs) can deliver prolonged exposure and relatively constant levels of the coupled therapeutic agents in the blood and tissues of the body. The thermally-activated SIPs can also achieve prolonged release of larger molecules, such as proteins and polypeptides. The therapeutic agent-coupled thermally-activated SIPs can be stable at or below room temperature, and can release the associated therapeutic agent when a triggering temperature of, for example, 37° C. is reached. The release of the therapeutic agent can occur at a fixed rate as repeating units to which the therapeutic agent is bound are released in a stepwise fashion from the polymer. Thus, each therapeutic agent molecule remains covalently attached to the polymer chain until queued for release. This can result in an approximately constant concentration of therapeutic agent in the plasma, which ultimately translates into approximately constant levels of therapeutic agents in the body's tissues.

In some embodiments, the therapeutic agent can be released simultaneously to the release of the repeating units, such that the rate of therapeutic agent release is substantially the same as the rate of release of the repeating units. In some embodiments, the therapeutic agent can be released subsequent to the release of the repeating units, such that the rate of therapeutic agent release is different from that of the repeating units.

Figure 4:
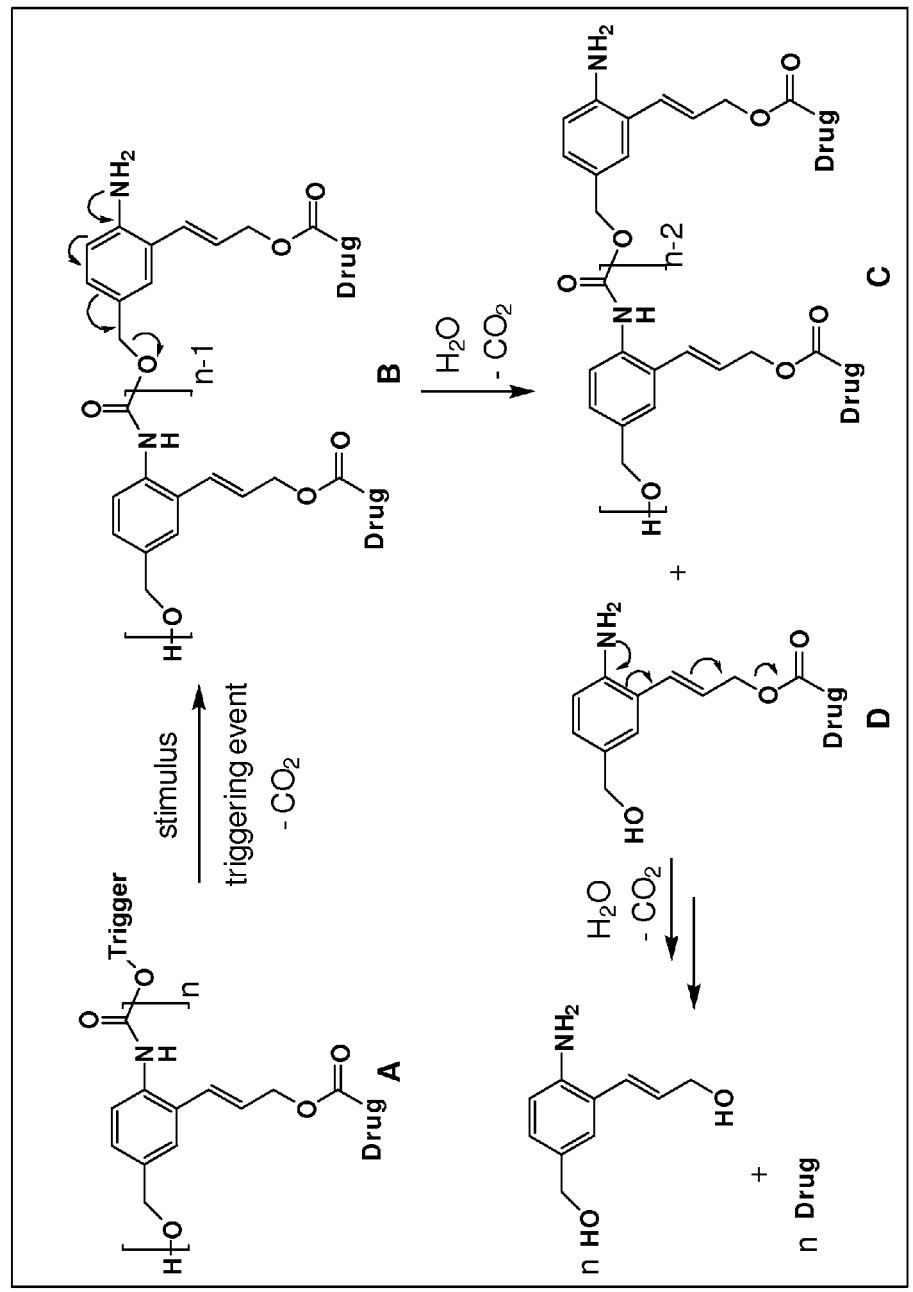
FIG. 4 is a schematic representation of an embodiment of a therapeutic agent (i.e., drug)-coupled thermally-activated self-immolative polymer.

A representative SIP activation, depolymerization, and therapeutic agent release is shown in FIG. 4. Referring to FIG. 4, upon triggering the SIP, the head end is converted to a highly electron-releasing amino functionality (A→B) that facilitates 1,6-elimination to detach the repeat unit at the terminus and liberate an active species on the remaining head end (C). Therapeutic agent release from the detached unit (D) is accomplished by a second elimination reaction. The depolymerization and concomitant therapeutic agent release events continue repetitively until all repeat units have been consumed. Examples 1 and 2 illustrate some embodiments of thermally-activated SIPs that can be used as drug delivery vehicles.

In some embodiments, 5-fluoruracil can be coupled to thermally-activated SIPs and administered to a subject parenterally. In some embodiments, buprenorphine can be used as a covalently bound therapeutic agent to a thermally-activated SIP to treat opiate addiction, where it can be administered (e.g., parenterally) with a relatively low risk of abuse. In some embodiments, the covalently-bound therapeutic agent can be

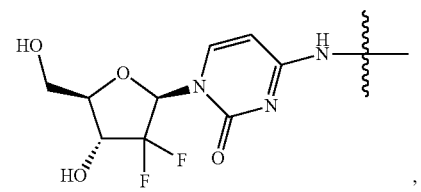

,

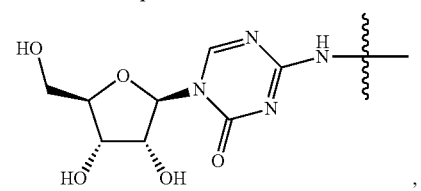

,

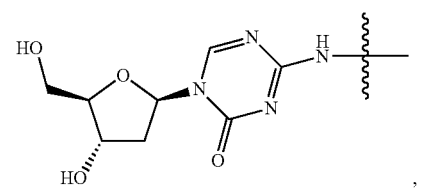

, and/or

-continued

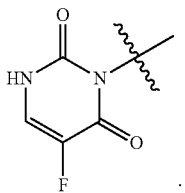

Degradable Materials

The depolymerization event itself can be a desired function of the SIP. Specifically, thermally-activated depolymerization can be used to irreversibly degrade hydrophobic components of micelles, nanoparticle frameworks, microcapsule shells, and solid patterned plastics. These degradable platforms can have applications in areas including drug delivery, self-healing materials (by release of small molecules that promote cross-linking, monomer polymerization, etc.), and lithography. Hydrolytic degradation of micelles formed from self-assembly of block copolymers including hydrophobic SIP blocks is described, for example, in DeWit et al., J. Am. Chem. Soc. 2009, 131:18327-18334, herein incorporated in its entirety.

Small molecule release can be achieved from degradable capsules that include SIPs as building blocks in a capsule (e.g., a microcapsule) shell, where degradation of the SIP releases the encapsulated small molecules. See, e.g., Esser-Kahn et al., J. Am. Chem. Soc. 2010, 132:10266-10268, herein incorporated in its entirety. Quantitative SIP deconstruction may not be necessary for nearly complete release of the encapsulated contents in a capsule that includes SIPs as building blocks. Thus, content release can be achieved in shorter time spans than those required for complete SIP depolymerization.

Thermally-activated depolymerization of SIPs in the solid-state can be used in lithographic processes. See, e.g., Seo et al., J. Am. Chem. Soc. 2010, 132:9234-9235. For example, a plastic film can be prepared from a thermally-activated self-immolating polymer, and the film can be selectively depolymerized at locations where a triggering temperature is provided by localized heating. The resulting film can have a particular pattern, where the heated areas are substantially free of the thermally-activated self-immolating polymer. In some embodiments, the thermally-activated self-immolating polymer is applied over a substrate, and the substrate can be heated at selected locations to trigger the depolymerization of the thermally-activated self-immolating polymer at the selected locations. Areas that are not heated can retain the thermally-activated self-immolating polymer. In some embodiments, a substrate can have a surface that includes the thermally-activated self-immolating polymer in a predetermined pattern and one or more materials in areas not covered by the thermally-activated self-immolating polymer. Upon heating of the substrate, the thermally-activated self-immolating polymer can depolymerize, and the areas not covered by the thermally-activated self-immolating polymer can remain.

EXAMPLES

Example 1

Synthesis and Mechanistic Studies of Thermally-Activated SIPs

The extent to which carbamoylnitroso species are able to trigger the depolymerization of SIPs was determined. The synthesis and stability of small molecule cycloaddition adducts derived from functionalized dienes, including anthracenes and cyclopentadienes was established. The synthesis and stability of cycloaddition adducts at the triggering position of SIPs was established. The extent to which such adducts can trigger the depolymerization of SIPs was determined. Water-soluble variants capable of releasing small molecules upon activation and self-immolation were prepared and evaluated.

Trigger Moieties and Thermally-Activated Depolymerization

Carbamoylnitroso species released upon cycloreversion are capable of liberating an electron rich species, ultimately triggering depolymerization of the SIP. Here, carbamoylnitroso species were generated at the chain end of SIPs, as shown in Scheme 4. Monomer 1 was prepared as described in Sagi, A. et al., J. Am. Chem. Soc. 2008, 130:5434-5435 and polymerized under basic conditions to produce SIPs with degrees of polymerization (DPs) of 8-10. Hydroxylamine was then added to the reaction mixture to install the desired end group as shown in polymer 2. This protocol typically produces samples with 87-90% of the end groups possessing the desired functionality. The resulting hydroxyurea-capped SIP 2 was subjected to tetrabutylammonium periodate (TBAP), a reagent used for oxidizing hydroxyureas to carbamoylnitroso species. Upon oxidation, the hydroxyurea decomposed to the aniline end group (SIP 3). Heating SIP 3 to 40° C. promoted the depolymerization, producing aminobenzyl alcohol (ABA) 4 as the terminal product. These results confirmed that carbamoylnitroso formation can be used to ultimately trigger SIP depolymerization.

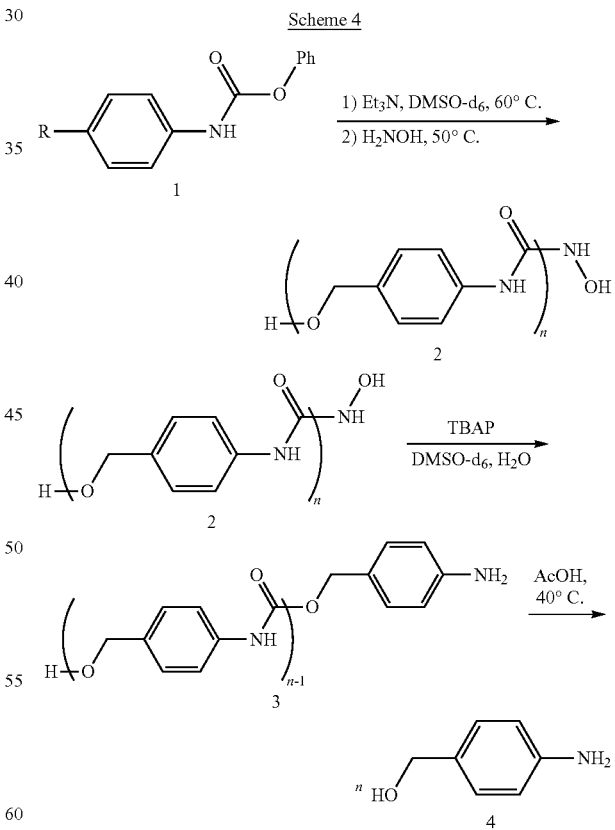

Scheme 4

Referring to Scheme 5, the cycloaddition reaction between small molecule hydroxyureas that could mimic the chain end of a SIP and functionalized anthracenes and cyclopentadienes was studied. In Scheme 5, TBS is tert-butyldimethylsilyl. Key data are summarized in Table 1.

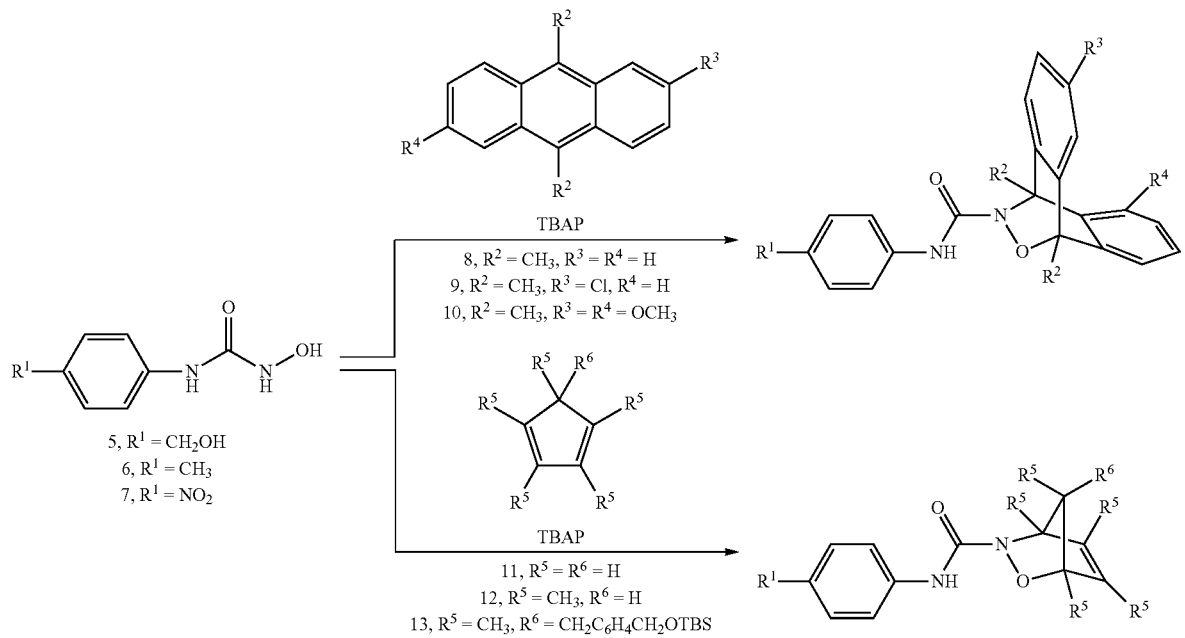

Scheme 5

Referring to Scheme 5 and Table 1, 4-nitrophenylhydroxyurea was used to explore the extent to which the substitution of the arene would influence adduct stabilities. The electron-withdrawing nitrophenyl substitution of the arene resulted in a slight increase in the thermal stability (entry 4). Cycloaddition adducts were formed with 9,10-DMA, and cycloreversion was typically found to occur below room temperature (RT) for many of these species (entries 1-4). Adducts were observed by ¹H NMR spectroscopy shortly after starting the reaction (within 1 h), and quickly decomposed, thus precluding isolation. Adduct formation was also monitored by thin-layer chromatography (TLC) to determine the temperature at which the cycloreversion was occurring. Numerous anthracenes with different substituents (i.e., electron donating or withdrawing groups) were screened for formation of cycloaddition adducts (data not shown). 9,10-DMA formed adducts were found to be the most stable.

TABLE 1

Data for different hydroxyurea/functionalized anthracene or cyclopentadiene combinations.

| Entry | Hydroxyurea | Diene | Temperature (° C.) | Solvent | Yield (%) | Cycloreversion Threshold (° C.) |
|---|---|---|---|---|---|---|
| 1 | 5 | 8 | RT | DMSO | 10 | <RT |
| 2 | 6 | 8 | RT | THF | 44 | <−78 |
| 3 | 6 | 8 | −78 | THF | 10 | <−78 |
| 4 | 7 | 8 | −78 | THF | 58 | <−41 |
| 5 | 5 | 11 | RT | THF/DMSO 1:0.3 | 54[d] | 70 |
| 6 | 6 | 11 | 0 | THF | 59[d] | 80 |
| 7 | 7 | 11 | −78 | THF | 19[d] | 80 |
| 8 | 6 | 12 | RT | THF | 31[d] | 70 |
| 9 | 6 | 13 | RT | THF | 17[d] | 100 |
| 10 | 2 | 8 | RT | DMSO/DCM 1:1 | 82[e] | <RT |
| 11 | 2 | 9 | RT | DMSO/DCM 1:0.75 | 51[e] | <RT |
| 12 | 2 | 10 | RT | DMSO/DCM 1:0.5 | 11[e] | <RT |
| 13 | 2 | 11 | RT | DMSO/DCM 1:0.8 | 55[e] | 90 |

Adducts derived from cyclopentadiene displayed greater thermal stability in comparison with those derived from anthracene (entries 5-9). The cyclopentadiene-based adducts were found to be stable to chromatography and thus able to be better isolated and characterized. These adducts were stable up to 40° C. for several hours, except for those containing pentamethylcyclopentadiene 12, which slowly underwent rearrangement to an unidentified product. Adducts formed from substituted cyclopentadiene 13 underwent similar decomposition as 12, but did not appear to do so below 90° C., as judged by $^1$H NMR spectroscopy.

Cycloaddition with SIP 2 also afforded adducts with 9,10-DMA. The adduct possessed enhanced stability in solution when conjugated to the polymer (activation over a period of several hours as opposed to minutes), facilitating isolation and characterization. The polymer with 9,10-DMA adduct was also stable at room temperature in the solid state. Numerous functionalized anthracenes were tested, and 9,10-dimethyl-substituted anthracenes yielded adducts (entries 10-12) that were persistent at room temperature, consistent with the small-molecule analogues described in Scheme 5. Cyclopentadiene was also found to form adducts on the chain end of SIP 2 (entry 13), and these adducts were found to have very high thermal stability for this series.

With SIPs capped with cycloaddition adducts in hand, the cycloreversion-triggered depolymerization of SIPs was tested. Thermal activation and depolymerization of SIP 14 is shown in Scheme 6. SIP 14 was heated at 37° C. in wet DMSO-d$_6$ (Scheme 6) and monitored by $^1$H NMR spectroscopy using 1,3,5-trimethoxybenzene as an internal standard (FIG. 2).

Figure 2:
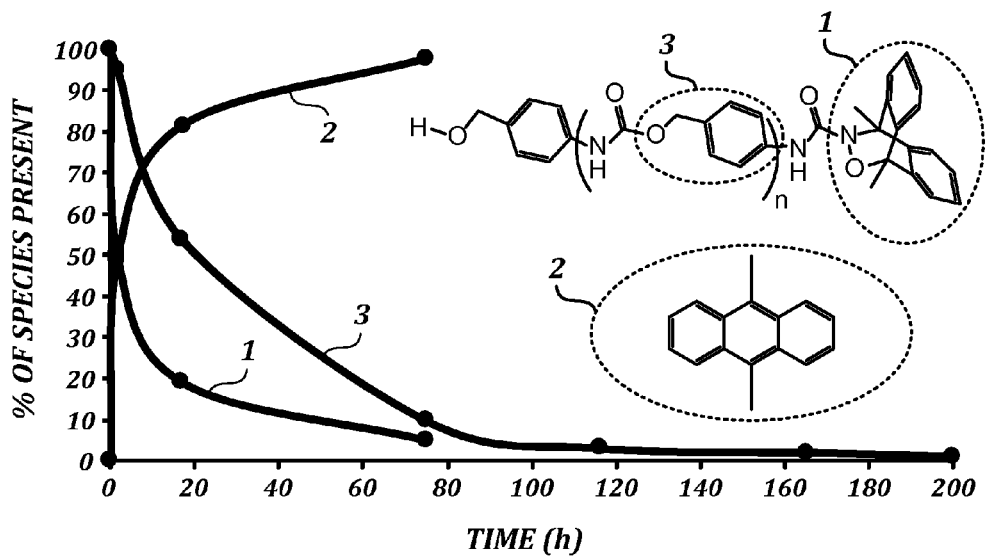
FIG. 2 is a graph showing reaction progress as determined by $^1$H NMR spectroscopy for the thermal activation and depolymerization of an embodiment of a thermally-activated self-immolative polymer, at 37° C. in DMSO-$d_6$ containing adventitious water or added $D_2O$, using 1,3,5-trimethoxybenzene as an internal standard.
Figure 3:
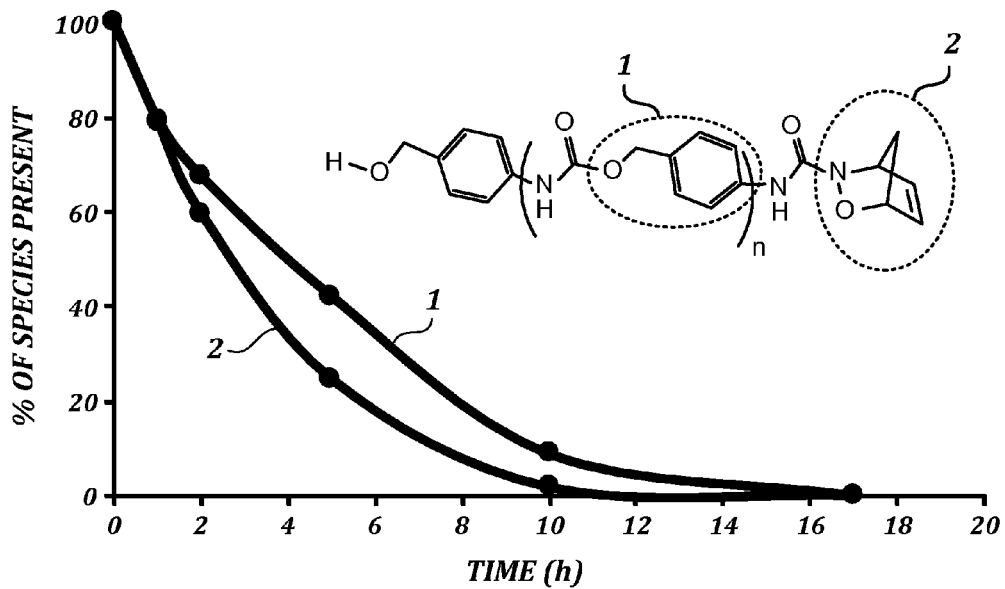
FIG. 3 is a graph showing reaction progress as determined by $^1$H NMR spectroscopy for the thermal activation and depolymerization of an embodiment of a thermally-activated self-immolative polymer at 85° C. in DMSO-$d_6$ containing adventitious water or added $D_2O$, using 1,3,5-trimethoxybenzene as an internal standard.

>80% conversion within 17 h, whereas depolymerization progressed over the course of 165 h (FIG. 2). The time required to achieve complete depolymerization is expected to scale with the DP of the SIP (i.e., longer polymer chains will take longer to reach full depolymerization). When heated to 60° C., complete cycloreversion of the trigger was observed within 20 min. Similar results were obtained from SIPs bearing trigger moieties derived from cyclopentadiene, but at higher temperatures. Specifically, the cyclopentadiene-based triggers were stable for >24 h at 50° C. At 85° C., cycloreversion and complete depolymerization was observed within 35 h (FIG. 3).

As a control experiment, SIP 16 was hydrogenated to yield SIP 17, which is unable to undergo cycloreversion (Scheme 7). Upon heating at 85° C. for 28 h, SIP 17 did not produce ABA and no changes in the $^1$H NMR spectrum were observed over the course of the experiment. This observation supports the proposed reactivity of the cycloaddition adducts and their function as thermal trigger moieties for SIPs.

Scheme 6

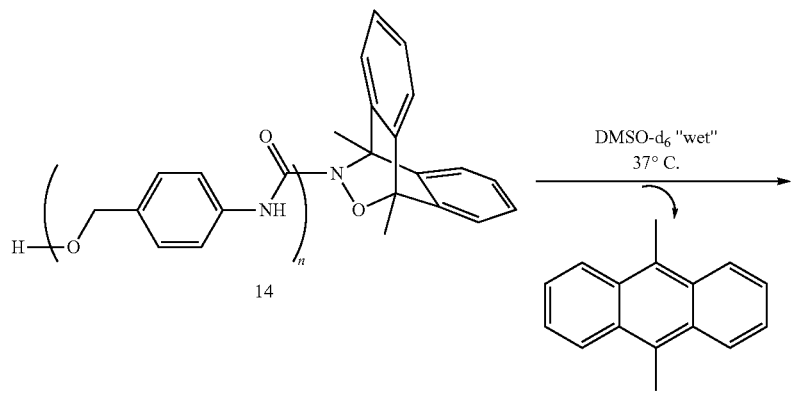

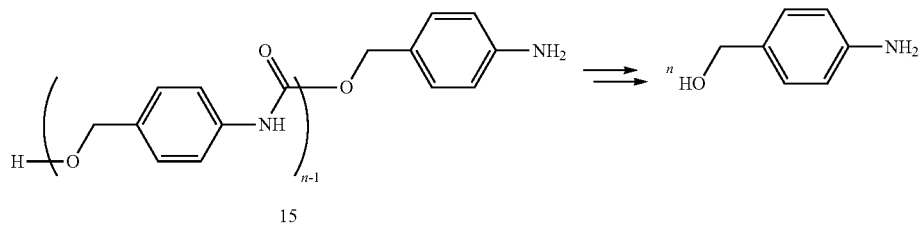

Referring to FIG. 2, the cycloreversion is indicated by the line 1 and shows the change in the amount of cycloaddition adduct end group (thermal trigger moiety) over time. The concomitant increase in the amount of 9,10-DMA (line 2) and correlation between the thermal trigger moiety and 9,10-DMA indicated that the cycloreversion process was proceeding with little or no byproducts being formed. That is, the conversion from thermal trigger moiety→9,10-DMA proceeds in nearly quantitative yield. Line 3 shows the relative amount of repeat unit originating from capped SIP chains remaining over time. The steady decrease is due to depolymerization following the thermal activation of the end group. Notably, the cycloreversion was found to achieve Scheme 7

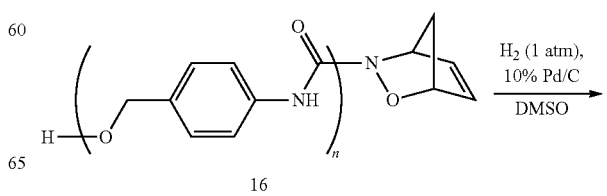

-continued

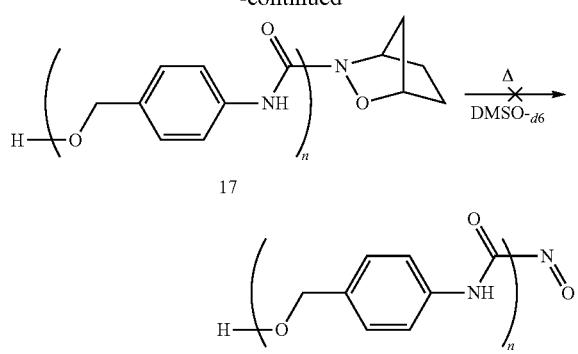

Water-Soluble, Thermally-Activated SIPs

Scheme 8 shows representative water-soluble building blocks and synthesis of a thermally-activated triblock copolymer containing an SIP middle block. Referring to Scheme 8, telechelic SIP was modified to have an alkyne end group capable of azide-alkyne "click" reactions (compound 18). To install the thermal trigger moiety, PDMA- and PEG-based polymers bearing anthracene or cyclopentadiene end groups were used. These end groups react in the same manner as that described in Scheme 5 to install the thermal trigger moiety and produce polymers such as 19 (Scheme 8). Since thermal activation of a polymer such as 19 would release the hydrophobic SIP block, a persistent water-soluble block was installed onto the SIP end group opposite the thermal trigger moiety. Polymers such as PDMA-N3 and PEG-N3 can each serve as coupling partners in the click reaction to provide triblock copolymers such as 20.

Scheme 8

Water-soluble polymers with end groups capable of conjugation with SIPs:

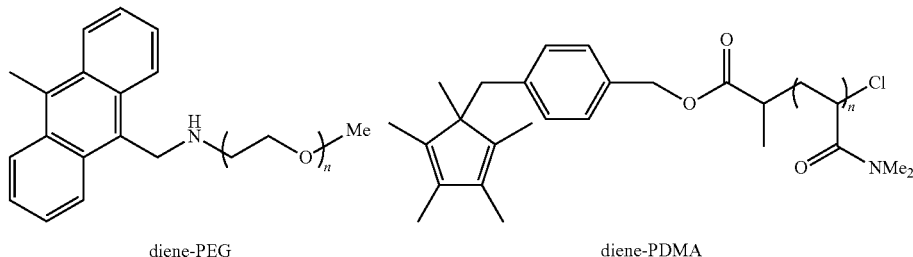

diene-PEG                    diene-PDMA

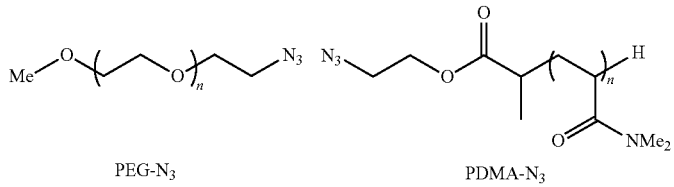

PEG-N$_3$                    PDMA-N$_3$

Representative synthesis of water-soluble triblock copolymers comprising SIP center blocks:

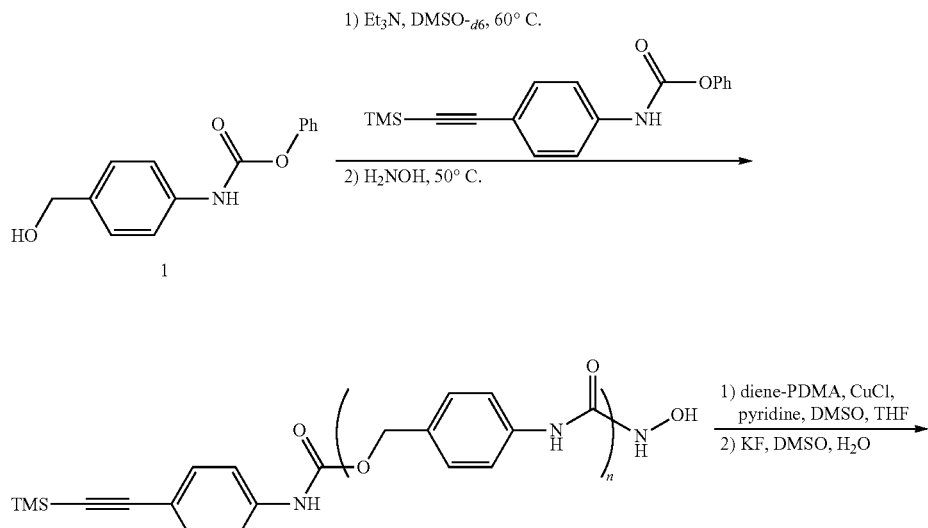

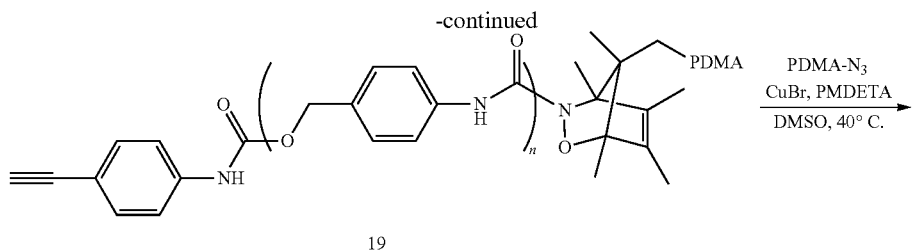

19

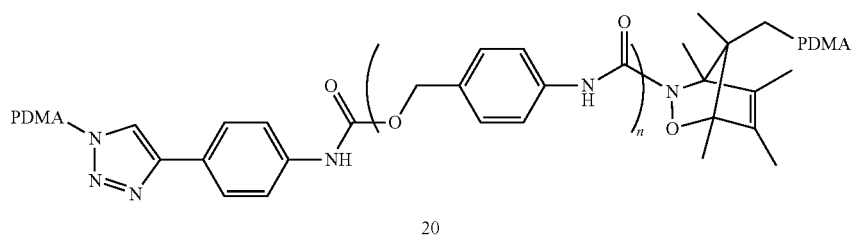

20

To demonstrate solubility, thermal activation, and depolymerization in aqueous environment, triblock copolymer 20 was dissolved in D$_2$O (10 mg/mL) and monitored via $^1$H NMR spectroscopy (Scheme 9). At ambient temperature, no depolymerization was observed for 48 h. Upon heating the solution to 100° C., thermal activation and depolymerization was observed with >95% of the SIP repeat units being liberated as 4-aminobenzyl alcohol within 24 h. Without wishing to be bound by theory, it is believed that more thermally-labile anthracene-based triggers can enable efficient activation near 37° C.

Development of Therapeutic Agent-Releasing Capabilities

To accomplish both depolymerization and release of small-molecule therapeutics, SIPs capable of linear depolymerization and side-chain release were prepared, as depicted in Scheme 10. Briefly, mono-protected diol 21 was synthesized according to Weinstain, R. et al., *Chem. Eur. J.* 2008, 14:6857-6861. Orthogonal protection using tert-butyldiphenylsilyl chloride (TBDPS-Cl) provided 22, and selective deprotection furnished monomer 23. Polymerization in the presence of Et$_3$N, followed by end group functionalization as before, yielded polymer 24 as a pivotal intermediate poised for conjugation with water-soluble exterior polymer blocks and therapeutic agent attachment.

Scheme 9

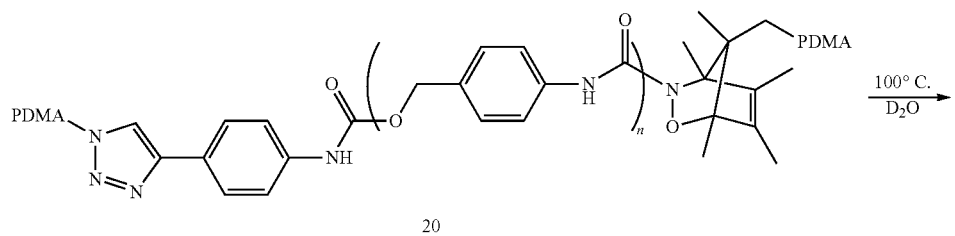

20

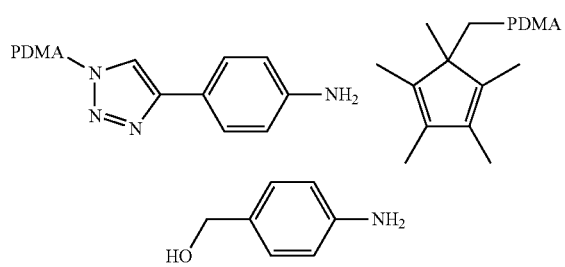

Scheme 10

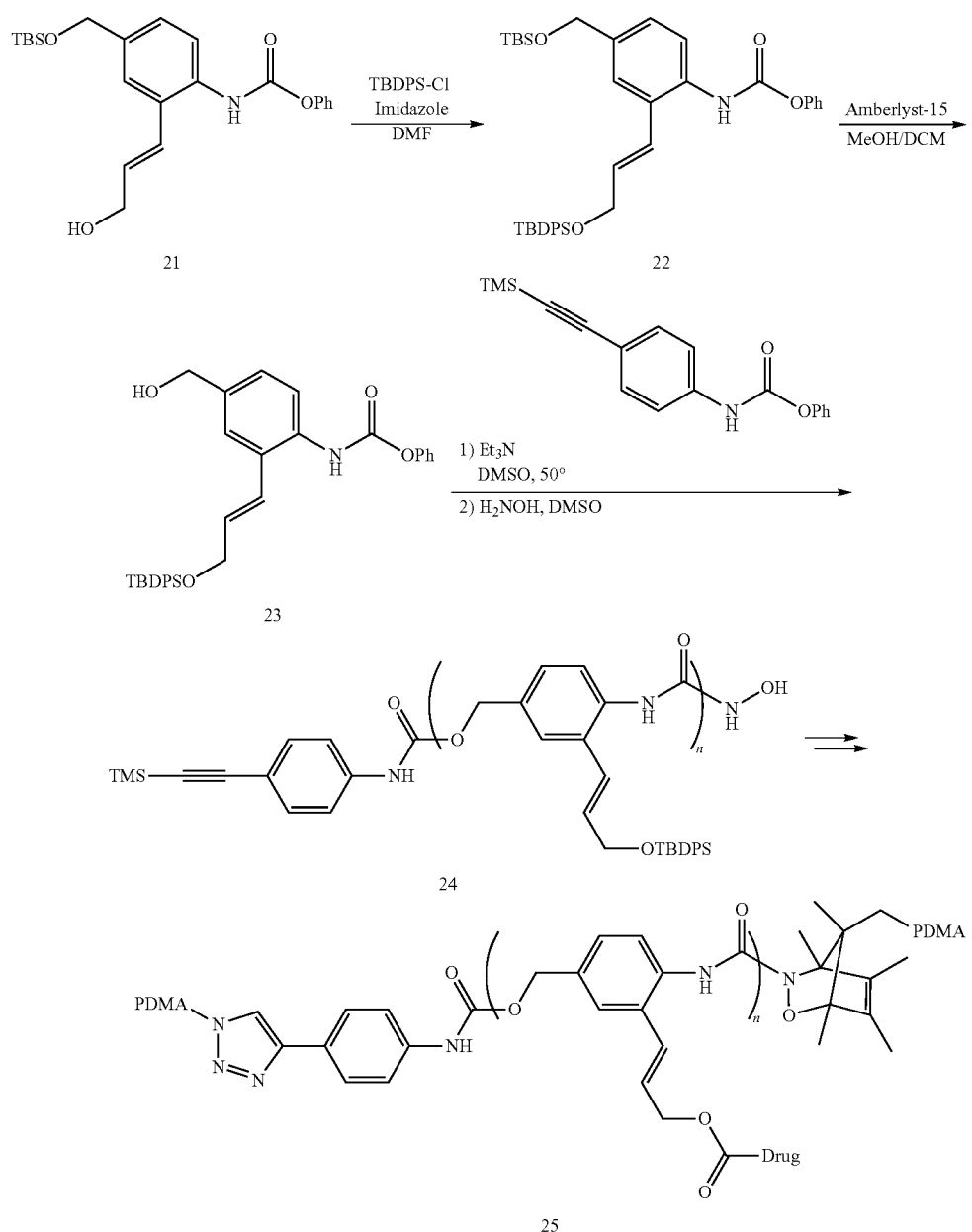

In summary, thermally-activated SIPs comprised of cycloaddition adducts between carbamoylnitroso end groups and various cyclic 1,3-dienes were developed. The trigger moieties react spontaneously at given, predictable temperature thresholds without the need for exogenous chemical additives. The SIP units can be rendered water-soluble and can be used in biological applications such as sustained release of therapeutic or theranostic agents.

Synthetic Procedures
Synthesis of Diene 13

To a solution of 4-(chloromethyl)benzyl alcohol (1.72 g, 11.0 mmol) in anhydrous methylene chloride (60 mL) under $N_2$ atmosphere at 0° C. was added tert-butyldimethylchlorosilane (TBS-Cl) (1.82 g, 12.1 mmol) and imidazole (0.97 g, 14.3 mmol). The reaction flask was stirred vigorously for 2 h. After 2 h, the product mixture was filtered, washed with saturated ammonium chloride and brine solutions. The organic layer was then filtered through a plug of silica gel using methylene chloride. The product—4-(chloromethyl)benzyloxy(tert-butyldimethyl)silane—was isolated after concentration under reduced pressure and was furnished as a while solid (2.72 g, 91% yield). This product was used in the next step as described below.

A solution of 1,2,3,4,5-pentamethylcyclopentadiene (0.635 g, 4.66 mmol) and tetra-n-butylammonium bromide (0.15 g, 0.47 mmol) in anhydrous THF (25 mL) was chilled to 0° C. under a $N_2$ atmosphere. A solution of n-BuLi (2.5 M in hexanes, 2.61 mL, 6.53 mmol) was added dropwise over 5 minutes. After 10 minutes more, the 4-(chloromethyl)benzyloxy(tert-butyldimethyl)silane (1.20 g, 4.43 mmol)

was added and the resulting mixture was stirred for 5 h. The reaction mixture was then diluted with ether. The organic layer was washed with deionized water followed by brine. It was then concentrated under reduced pressure to furnish the diene as an oil (1.48 g, 90% yield).

General Procedure to Form Small Molecule Adducts (from Dienes 8-13)

A flame-dried round-bottom flask under dry $N_2$ was charged with hydroxyurea (1.0 equiv), diene (1.5 equiv relative to hydroxyurea) and dry THF (hydroxyurea at 0.15 M) and the resulting solution was stirred at the temperature indicated in Table 1. In a separate flame-dried round-bottom flask, a stock solution of TBAP was prepared in dry THF (0.15 M). To the reaction flask was added TBAP solution (1.5 equiv of TBAP relative to hydroxyurea) dropwise via syringe. The reaction progress was monitored by TLC (20% EtOAc/hexanes). The reaction mixture was analyzed by $^1$H NMR spectroscopy when complete consumption of the hydroxyurea was observed by TLC.

General Procedure to Form Hydroxyurea-Capped SIP

A flame-dried round-bottom flask under dry $N_2$ was charged with monomer 1 (1.0 equiv) and a stir bar. Dry DMSO (monomer at 2.0 M) and dry $Et_3N$ (100 mol % relative to monomer) were then added. The solution was heated at 60° C. for 2.5 h. At that time, a small aliquot was removed and the DP was determined by $^1$H NMR spectroscopy by comparing the areas of the peaks corresponding to end groups and repeat units. To the reaction mixture was then added hydroxylamine (5.0 equiv relative to end group) from a 1.0 M stock solution prepared in dry DMSO. The resulting mixture was stirred for 6 h at 50° C. The reaction mixture was then poured into MeOH (approximately 10 times the volume of DMSO) and cooled in a refrigerator causing precipitation of the polymer. The precipitate was collected on a sintered-glass Büchner funnel and dried under vacuum. Technical note: the hydroxylamine solution was prepared by combining hydroxylamine hydrochloride with anhydrous $K_2CO_3$ (2.0 equiv relative to hydroxylamine hydrochloride) in dry DMSO (hydroxylamine at 1.0 M). The mixture was stored at room temperature for 12 h prior to use.

General Procedure to Install Thermal Trigger Moieties onto SIPs

A flame-dried round-bottom flask under dry $N_2$ was charged with SIP 2 (1.0 equiv), diene (5.0 equiv relative to SIP) and a stir bar. Dry DMSO and dry DCM were then added (the ratio of solvents were optimized for diene solubility with the SIP at 30 mM). TBAP (1.0 equiv relative to SIP) was added portionwise over 4 30-min intervals, at which point the remaining TBAP was then added (2.0 equiv total relative to SIP). After 6 h from the first TBAP addition, the reaction mixture was poured into MeOH (approximately 10 times the volume of DMSO) and cooled in a refrigerator causing precipitation of the polymer. The precipitate was collected on a sintered-glass Büchner funnel, washed with DCM, and dried under vacuum.

General Procedure for Thermal Decomposition Studies

The SIP with the installed thermal trigger moiety (1.0 equiv) was dissolved in DMSO-$d_6$ and transferred to a NMR tube. As an internal standard, 1,3,5-trimethoxybenzene (0.5 equiv) was also added. The NMR cap was sealed with electrical tape and a time-zero NMR spectrum was collected at room temperature. The NMR tube was then immersed in a pre-heated oil bath set to the desired temperature and the thermal decomposition progress was monitored at various time points by $^1$H NMR spectroscopy.

A flame-dried round-bottom flask was charged with 4-iodoaniline (26, 1.0 equiv) and a stir bar then brought into a glove box. $PdCl_2(dppf)$ (0.03 equiv) and CuI (0.06 equiv) were added to the flask. The solids were then dissolved in THF (26 at 0.1 M) and $Et_3N$ was added (1 mL per mmol of 4-iodoaniline). Trimethylsilylacetylene (1.1 equiv) was then added and the flask was sealed with a septum and electrical tape and then protected from light by wrapping the flask in aluminum foil. The reaction was stirred at room temperature for 24 h. The reaction mixture was then filtered through a plug of silica gel and concentrated under reduced pressure. The crude solid was dissolved in $CH_2Cl_2$ and washed with water, then brine, and dried with $Na_2SO_4$. The solvent was removed and the product was dried under vacuum to provide the desired product (27) in 95% yield.

From the previous reaction, 4-(trimethylsilylethynyl)aniline (27, 1.0 equiv) was dissolved in a 2:1:2 mixture of THF, water, and sat. $NaHCO_3$ by volume (aniline substrate at 0.5 M). Phenyl chloroformate (1.2 equiv) was then added slowly over 5 min while stirring. The reaction was monitored by TLC and was completed in 3.5 h. The reaction mixture was diluted with EtOAc and washed with sat. $NH_4Cl$, sat $Na_2CO_3$, water, and brine. The organic layer was separated and dried with $Na_2SO_4$. The solvent was removed under vacuum. The product was then recrystalized from a EtOAc/hexane mixture giving 28 in 87% yield (Scheme 11).

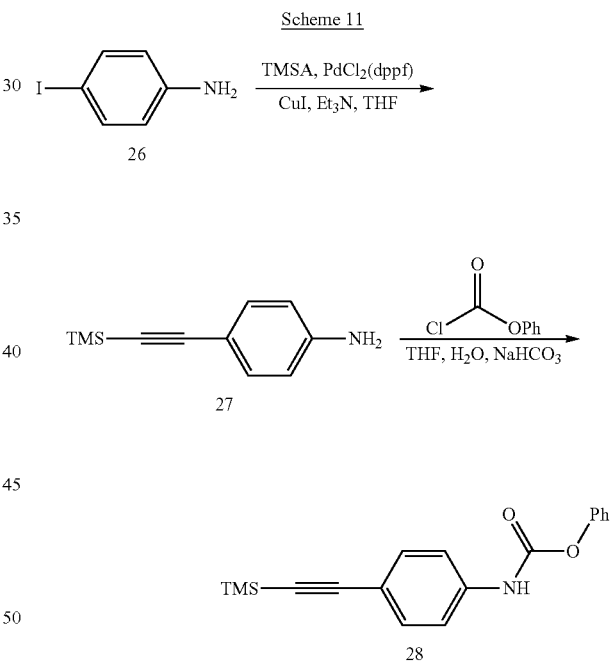

Scheme 11

Synthesis of TMS-Protected Alkyne/Hydroxyurea Capped SIP 18

To a flame dried flask was added monomer 1 (1.0 equiv) and alkyne 28 (0.2 equiv) under $N_2$ purge. Dry DMSO (1 at 2.0 M) and $Et_3N$ (1.0 equiv) were then added. The solution was stirred and heated at 60° C. for 4 h. An additional 0.05 equiv of 28 was then added to the reaction solution and heating was continued for another 2 h. Hydroxylamine (1.0 equiv) from a 1.0 M stock solution prepared in dry DMSO was then added via syringe and the resulting mixture was stirred for 6 h at 50° C. The reaction mixture was then poured into MeOH (approximately 10 times the volume of DMSO) and cooled in a refrigerator causing precipitation of the polymer. The precipitate was collected on a sintered-glass Büchner funnel and dried under vacuum. Technical note: the hydroxylamine solution was prepared by combining hydroxylamine hydrochloride with anhydrous $K_2CO_3$ (2.0 equiv relative to hydroxylamine hydrochloride) in dry DMSO (hydroxylamine at 1.0 M). The mixture was stored at room temperature for 12 h prior to use.

Synthesis of SIP-PDMA Diblock Copolymer 19

PDMA bearing a pentamethylcyclopentadiene end group (1.0 equiv) and SIP 18 (10 equiv) were combined in a flame dried flask under $N_2$. Dry DMSO and dry THF (2:1 v/v, PDMA at 80 mg/mL) were each added via syringe, and then CuCl (0.5 equiv) and pyridine (0.1 equiv) were added. The solution was stirred at room temperature for 16 h. The solution was then diluted with THF to ca. 3-fold dilution, and filtered through a plug of alumina. The polymer solution was concentrated under vacuum and then redissolved in a minimal amount of EtOAc and precipitated into diethyl ether (approximately 10 times the volume of EtOAc). The precipitate was collected on a sintered-glass Büchner funnel and dried under vacuum giving the product in 60% yield. GPC analysis revealed a weight-average molecular weight ($M_W$) of 49 kDa (PDI=1.1).

The diblock copolymer produced in the preceding reaction (1.0 equiv) was combined with KF (15.0 equiv) in DMSO (diblock at 140 mg/mL) and water (5% by volume) in a screw cap vial. The reaction solution was stirred for 3.5 h at room temperature. The solution was then diluted with THF (ca 3-fold dilution) and diethyl ether was added until the polymer precipitated onto the sides of the vial. The ether layer was decanted and the polymer residue was dissolved in a minimal amount of THF and precipitated into ether (approximately 10 times the volume of THF). The precipitate was collected on a sintered-glass Büchner funnel and dried under vacuum giving 19 in 63% yield.

Synthesis of PDMA-SIP-PDMA Triblock 20

In a glove box, CuBr (10.0 equiv) and N,N,N',N'',N''-pentamethyldiethylenetriamine (PMDETA, 10.0 equiv) were dissolved in dry DMSO (CuBr at 0.01 M). This solution was then added to the deprotected SIP-PDMA diblock 19 (1.0 equiv) and PDMA-$N_3$ (1.0 equiv) in a screw cap vial. The vial was sealed with a Teflon-lined cap and the solution was heated at 40° C. for 24 h. The solution was then diluted with THF (ca. 3-fold dilution) and diethyl ether was added until the polymer precipitated onto the sides of the vial. The ether layer was decanted and the polymer residue was redissolved in a minimal amount of THF. The solution was then filtered through a plug of alumina and concentrated under reduced pressure. The crude material was then dissolved in a minimal amount of EtOAc and precipitated into diethyl ether (approximately 10 times the volume of EtOAc). The precipitate was collected on a sintered-glass Büchner funnel and dried under vacuum. Product obtained as a mixture of the starting polymers and ~40% of the desired triblock copolymer 20. GPC analysis revealed a $M_W$ of 65 kDa (PDI=1.1).

Thermal Activation of the PDMA-SIP-PDMA Triblock Copolymer 20 (Scheme 9)

The triblock copolymer (20) was dissolved in $D_2O$ (30 mg/mL) in an NMR tube. The tube was capped and sealed with electrical tape. A time-zero $^1H$ NMR spectrum was collected. The NMR tube was then immersed in a pre-heated oil bath set to 100° C. and the reaction progress was monitored in via $^1H$ NMR spectroscopy until depolymerization was complete.

Synthesis of Carbamate 22

To a solution of compound 21 (76 mg, 0.18 mmol) and imidazole (13 mg, 0.19 mmol) in DMF (2.0 mL) under $N_2$ atmosphere was added TBDPS-Cl (50 µL, 0.19 mmol) via syringe. The solution was stirred at room temperature and monitored via TLC (40% EtOAc/hexanes). After 2 h, the reaction was diluted with EtOAc (10 mL) and washed successively with saturated ammonium chloride solution (2×20 mL) and then with brine (2×10 mL). The organic layer was dried with $MgSO_4$ and concentrated under reduced pressure. The residue was purified by column chromatography (20% EtOAc/hexanes) to yield compound 22 as an orange-yellow solid (30 mg, 26% yield).

Synthesis of Monomer 23

Compound 22 (30 mg, 0.046 mmol) was dissolved in 3:1 MeOH:DCM (1 mL) and stirred vigorously. To this solution was then added Amberlyst 15—dry (20 mg). The reaction was monitored via TLC (40% EtOAc/hexanes). After 3.5 h the Amberlyst was removed via filtration through a pad of Celite and the volatiles were removed under reduced pressure. The residue was purified by column chromatography (80% EtOAc/hexanes) to yield monomer 23 as a white solid (11 mg, 45% yield).

Synthesis of Polymer 24

To a solution of compound 23 (11 mg, 0.021 mmol) in dry DMSO-$d_6$ (0.5 mL) under $N_2$ atmosphere was added $Et_3N$ (4 µL, 0.029 mmol). The reaction flask was sealed with a rubber septum and heated to 50° C. Reaction progress was monitored via $^1H$ NMR spectroscopy. After 3.5 h, the reaction mixture was added dropwise into an excess of MeOH causing precipitation of the desired polymer. The product was collected via vacuum filtration, rinsed with MeOH, and dried under vacuum to provide polymer 24 in 95% yield.

Example 2

Thermally-Activated SIPs as Drug Delivery Vehicle

Scheme 12 shows a synthesis of a thermally-activated SIP that can be used as a drug delivery vehicle. To impart water-solubility and increased biocompatibility poly(ethylene glycol) (PEG) is attached to the tail end of the SIP. Subsequently, the diblock copolymer will be functionalized with hydroxylamine to provide 30, and then subjected to oxidation and in situ trapping with various dienes. Finally, global deprotection will provide polyol 31 that can be readily conjugated with drug candidates.

Scheme 12
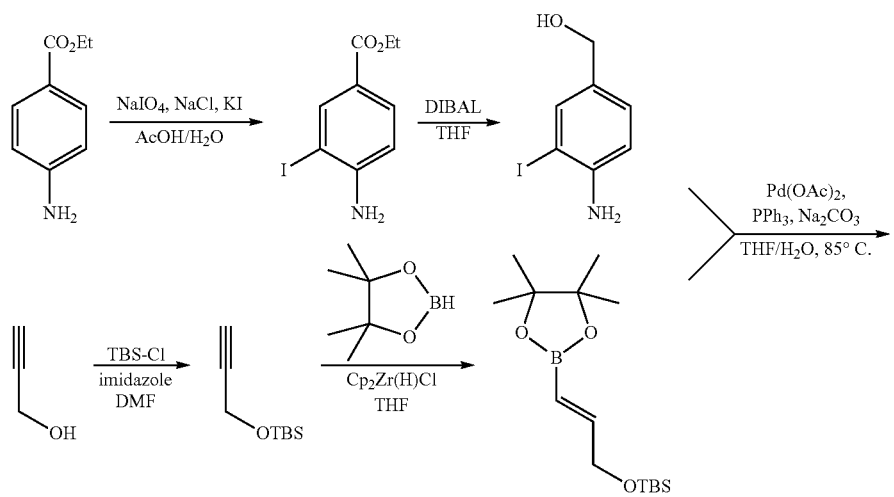
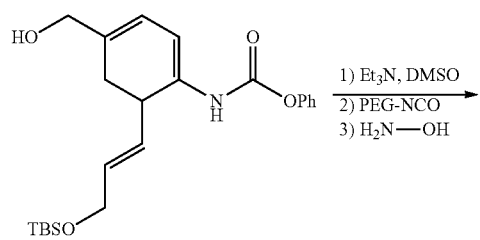
Synthesis of Drug-Ready SIP:
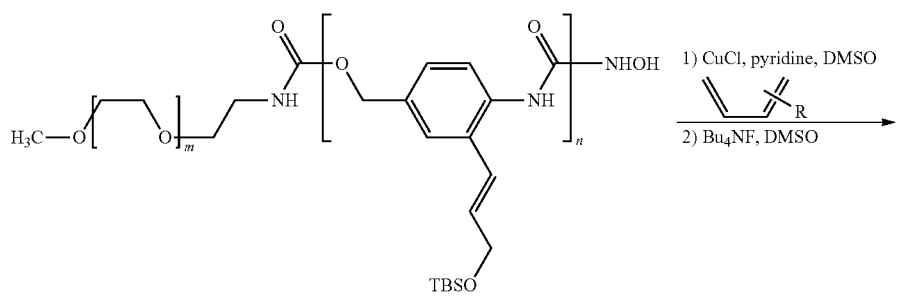

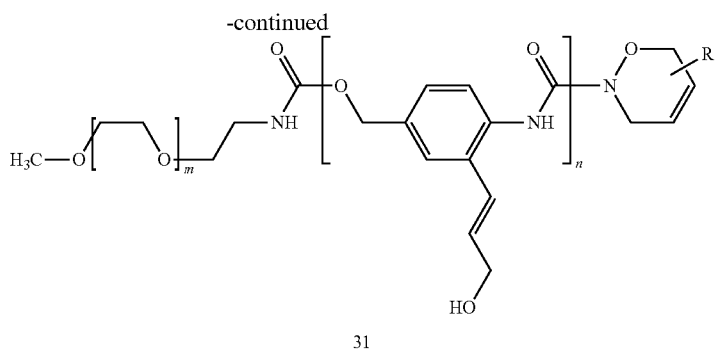

31

Example 3

Polymers Including Cyclopentadine-Based Oxazine Trigger Moieties

A diblock copolymer (Scheme 13) was prepared with disparate solubility from polymer 2 of Example 1. Initiator 32 was prepared from pentamethylcyclopentadiene and used for atom-transfer radical polymerization of N,N-dimethyl-acrylamide, providing poly(N,N-dimethylacrylamide) PDMA 33 ($M_w$=27.8 kDa, PDI=1.07). Treatment of 33 with an excess of 2 (10:1 mole ratio) under oxidative conditions provided complete end capping of 33 to yield diblock copolymer 34. Removal of residual 2 was accomplished by precipitation into methanol followed by filtration through Celite/alumina. GPC and $^1$H NMR analysis supported the successful 1:1 conjugation of the SIP and PDMA blocks. To evaluate the extent to which hydrolysis may be giving rise to background triggering of the SIP, control polymer 35 was prepared in which the trigger moiety is incapable of forming a carbamoylnitroso group.

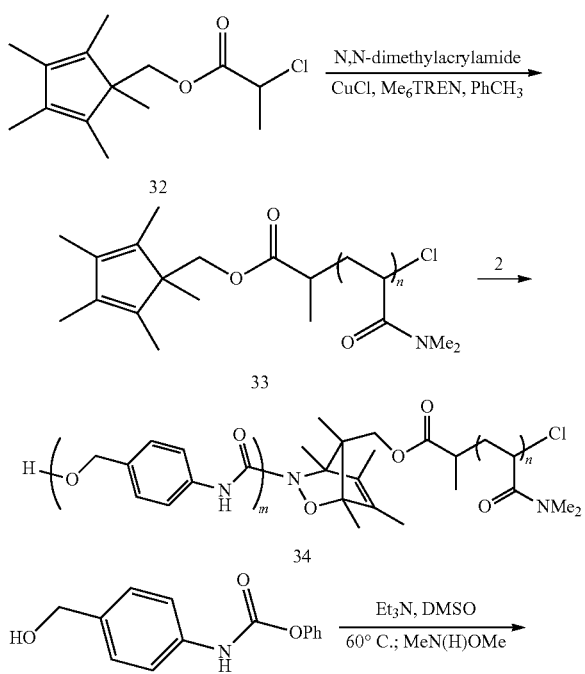

Scheme 13

Figure 5:
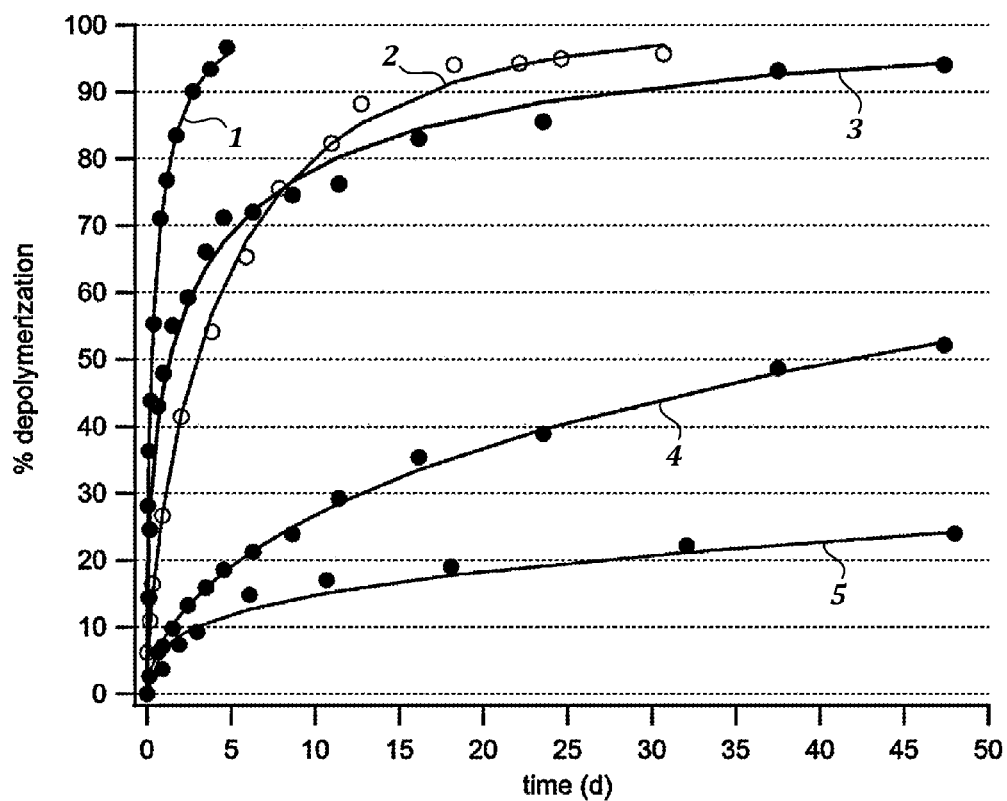
FIG. 5 is a graph showing reaction progress as determined by $^1$H NMR spectroscopy for the thermal activation and depolymerization of embodiments of thermally-activated self-immolative polymers at 85° C., 60° C., 40° C., and room temperature ("RT").

Thermal triggering and depolymerization experiments in DMSO-$d_6$/$D_2$O mixtures (9:1 v/v) of SIPs 34 and 35 were conducted. FIG. 5 shows the thermal activation and depolymerization of SIPs 34 (filled circles, line 1) and 35 (empty circles, line 2) in DMSO-$d_6$/$D_2$O (9:1 v/v) at 85° C., 60° C. (line 3), 40° C. (line 4), and RT (line 5), average of two runs. The % depolymerization was equal to 100–% SIP repeat units remaining, as determined by $^1$H NMR spectroscopy using 1,4-dicyanobenzene as an internal standard. The initial concentration of SIP repeat units was 7 mM. Initial average DPs of 34 and 35 were ca. 10-11 for each sample, as determined by $^1$H NMR spectroscopy. The curves were fit a modified Avrami equation.

Referring to FIG. 5, SIP depolymerization manifests a pseudo-zero order process, since the concentration of chains (and therefore active chain ends) does not decrease until chains have fully depolymerized. Activation of the trigger introduces a first-order dependence to the overall process. Thus, the ensemble kinetics of SIP activation and depolymerization is dependent upon the DP of the SIP block as well as the relative rates of each contributing event. A modified Avrami equation is a practical way to model the empirical depolymerization data for SIPs. In particular, fitting the depolymerization data to Equation (1), in which $P_0$ and P are the initial and time-dependent amounts of SIP, respectively, provides constants k and α.

$$P=P_0 e^{-(kt)^\alpha}$$ Equation (1)

The constants k and α have been referred to as an effective rate constant and adjustment factor related to the reaction order, respectively. The two constants can be used to accurately describe the depolymerization kinetics, and thus in combination are useful for comparison with other SIP depolymerizations (or kinetically similar processes).

Applying this method to the data in FIG. 5 (solid lines represent curve fits) yielded k and α values as summarized in Table 2. Comparison of the overall rate constants further suggested that the thermal trigger design can provide a good approach for on-demand activation of SIPs. Specifically, the rate constant at 85° C. is roughly 140-fold greater than at 40° C., and 3,800-fold greater than at room temperature ("RT"). Using the effective rate constants at each temperature, an activation energy of 27.0±2.5 kcal/mol was calculated for the overall activation and depolymerization process. Finally, the adjustment factors ranged from 0.34 to 0.56 for 34, which were consistent with SIPs thought to undergo depolymerization via combined first and zero order processes.

TABLE 2

Effective rate constants and adjustment factors for the depolymerization of SIPs 34 and 35[a]

| entry | SIP | temp (° C.) | k (h$^{-1}$) | α |
|---|---|---|---|---|
| 1 | 34 | RT | $1.9 \times 10^{-5}$ | 0.34 |
| 2 | 34 | 40 | $5.2 \times 10^{-4}$ | 0.56 |
| 3 | 34 | 60 | $1.2 \times 10^{-2}$ | 0.40 |
| 4 | 34 | 85 | $7.3 \times 10^{-2}$ | 0.54 |
| 5 | 35 | 85 | $8.4 \times 10^{-3}$ | 0.69 |

[a]Depolymerization data was fit to a modified Avrami equation using nonlinear regression analysis in IgorPro.

At a long-term storage temperature of 4° C. negligible activity from 34 was observed in solution over the course of 50 d. At RT, however, gradual activation leading to 24% depolymerization after 48 d was observed (FIG. 5). As expected, at 40° C. more rapid activation and depolymerization was observed, reaching 52% depolymerization after ca. 48 d. At 60 and 85° C., nearly full depolymerization was observed after ca. 47 and 5 d, respectively. 7% depolymerization was observed when 35 was heated at 40° C. for 47 d, and essentially no depolymerization at RT. Even at 85° C., the rate of depolymerization was much less for 35 than for the oxazine trigger variant (10), consistent with different mechanisms of activation between the two (Table 2, entries 4 and 5).

Additional confirmation of the oxazine trigger reactivity was obtained from thermolysis of 34 in the presence of excess 1,3-cyclohexadiene. Specifically, heating 34 at 60° C. in DMSO-d$_6$/D$_2$O (9:1 v/v) containing 300 equiv (ca. 1.7% by volume) of 1,3-cyclohexadiene relative to oxazine trigger significantly suppressed the rate of depolymerization. Only 20% depolymerization was observed after 2 d, versus nearly 60% for 34 at the same time and temperature. These results are consistent with the intermediacy of a carbamoylnitroso species and formation of the more thermally stable cyclohexadiene adduct. $^1$H NMR analysis also revealed increasing intensities of resonances centered at δ=4.80 ppm that were consistent with bridgehead protons of the cyclohexadiene-based oxazine.

Synthesis

Dry DMSO, THF, toluene, and CH$_2$Cl$_2$ were obtained from a Glass Contour solvent purification system. Et$_3$N and DMA were distilled after drying over CaH$_2$ overnight. TBAP was dried with PtO$_5$ overnight before use. House N$_2$ was passed through a drying tube before use. All other reagents and solvents were used as obtained from commercial sources. $^1$H and $^{13}$C NMR spectra were recorded on a Bruker AVance 300 and 500 MHz spectrometers. Chemical shifts are reported in delta (δ) units, expressed in parts per million (ppm) downfield from tetramethylsilane using the residual protio-solvent as an internal standard (CDCl$_3$, $^1$H: 7.26 ppm and $^{13}$C: 77.16 ppm; DMSO-d$_6$, $^1$H: 2.50 ppm and $^{13}$C: 39.5 ppm). GPC setup consisting of: a Shimadzu pump, 3 in-line columns, and Wyatt light scattering and refractive index detectors with 0.01 M LiBr in DMF as the mobile phase.

ABBREVIATIONS

DMA=N,N-dimethylacrylamide, DMSO=dimethylsulfoxide, DP=degree of polymerization, EDTA=ethylenediaminetetraacetic acid, PDMA=poly(N,N-dimethylacrylamide), RT=room temperature, SIP=self-immolative polymer, TBAP=tetrabutylammonium periodate, THF=tetrahydrofuran.

General Method for Oxidation Experiments with SIP 2 (Scheme 14)

SIP 2 (15 mg, 0.011 mmol, 1.0 equiv) was dissolved in anhydrous DMSO-d$_6$ (0.45 mL) under a N$_2$ atmosphere and transferred to a NMR tube. TBAP (7 mg, 0.016 mmol, 1.5 equiv), 1,3,5-trimethoxybenzene (0.7 mg, 0.0042 mmol), and D$_2$O (0.05 mL) were added and the NMR tube was capped and sealed with electrical tape. The sample was then heated at 40° C. and the depolymerization was monitored by $^1$H NMR spectroscopy. Control experiments without TBAP or D$_2$O were also completed.

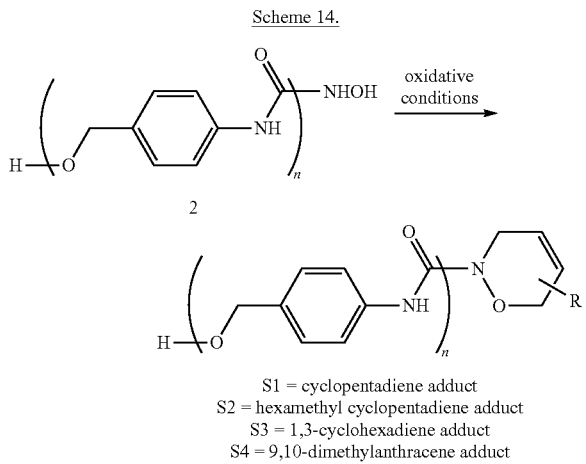

Scheme 14.

S1 = cyclopentadiene adduct
S2 = hexamethyl cyclopentadiene adduct
S3 = 1,3-cyclohexadiene adduct
S4 = 9,10-dimethylanthracene adduct Synthesis of SIP S1

Into a flame-dried round-bottom flask, SIP 2 (500 mg, 0.29 mmol, 1 equiv) was dissolved in dry DMSO (5 mL). Once dissolved, THF (1.5 mL) and freshly cracked cyclopentadiene (1.47 mL, 17.4 mmol, 60 equiv) were added. Finally, CuCl (6 mg, 0.058 mmol, 0.2 equiv) and pyridine (1 µL, 0.013 mmol, 0.05 eq.) were added to the solution. The reaction mixture was stirred (open to air) at RT for 18 h. The polymer solution was precipitated into CH$_2$Cl$_2$ (approximately 10 times the volume of DMSO) and the precipitate was collected on a sintered-glass Büchner funnel. The product was obtained in 80% yield with 55% of the chain ends bearing the desired adduct (as determined by $^1$H NMR spectroscopy by comparing integrations of each chain end).

Synthesis of SIP S2

A flame-dried round-bottom flask was charged with SIP 2 (25 mg, 0.018 mmol, 1.0 equiv), 1,2,3,4,5,5-hexamethyl-1,3-cyclopentadiene (134 mg, 0.892 mmol, 50 equiv) and a stir bar. The mixture was dissolved in dry DMSO (0.4 mL) and THF (0.3 mL). CuCl (1 mg, 0.01 mmol, 0.6 equiv) and pyridine (1 µL, 0.6 equiv) were then added. After 16 h of stirring (open to air) at RT, the reaction mixture was poured into MeOH (approximately 10 times the volume of DMSO) and cooled in a refrigerator causing precipitation of the polymer. The precipitate was collected on a sintered-glass Büchner funnel, washed with CH$_2$Cl$_2$ and dried under vacuum. The product was obtained in 65% yield with 60% of the chain ends bearing the desired adduct (as determined by $^1$H NMR spectroscopy by comparing integrations of each chain end).

Synthesis of SIP S3

A flame-dried round-bottom flask was charged with SIP 2 (100 mg, 0.091 mmol, 1.0 equiv), 1,3-cyclohexadiene (0.36 mL, 4.55 mmol, 50 equiv) and a stir bar. The mixture was dissolved in dry DMSO (1.6 mL) and THF (0.4 mL). CuCl (7.12 mg, 0.072 mmol, 0.8 equiv) and pyridine (1.45 µL, 0.2 equiv) were then added. After 16 h of stirring (open to air) at RT, the reaction mixture was poured into MeOH (approximately 10 times the volume of DMSO) and cooled in a refrigerator causing precipitation of the polymer. The precipitate was collected on a sintered-glass Büchner funnel, washed with $CH_2Cl_2$ and dried under vacuum. The product was obtained in 65% yield with 60% of the chain ends bearing the desired adduct (as determined by $^1$H NMR spectroscopy by comparing integrations of each chain end). To evaluate the thermal stability of the trigger, a solution of S3 in DMSO-$d_6$/$D_2$O (9:1 v/v) was heated at 60° C. and monitored by $^1$H NMR spectroscopy using 1,4-dicyanobenzene as an internal standard. At 140 h, 25% depolymerization was observed. For comparison, SIP 10 shows 72% depolymerization at 60° C. over the same time period.

Synthesis of SIP S4

A flame-dried round-bottom flask was charged with SIP 2 (35 mg, 0.023 mmol, 1.0 equiv), 9,10-dimethylanthracene (24 mg, 0.12, 5.0 equiv) and a stir bar. Dry DMSO (0.9 mL) and dry $CH_2Cl_2$ (0.6 mL) were then added. TBAP (20 mg, 0.047 mmol, 2 equiv) was added portion wise for the first equivalent over four 30-min intervals, at which point the remaining equivalent of TBAP was then added. After 6 h from the first TBAP addition, the reaction mixture was poured into MeOH (approximately 10 times the volume of DMSO) and cooled in a refrigerator causing precipitation of the polymer. The precipitate was collected on a sintered-glass Büchner funnel, washed with $CH_2Cl_2$, and dried under vacuum. The product was obtained in 71% yield with 99% of the chain ends bearing the desired adduct (as determined by $^1$H NMR spectroscopy by comparing integrations of each chain end).

Synthesis of S5

To a flame-dried, $N_2$-purged three neck round-bottom flask, fit with a condenser, was added paraformaldehyde (580 mg) and dry THF (10.5 mL). The resulting suspension was refluxed under $N_2$ for 2 h and then cooled to RT. To a separate flame-dried, $N_2$-purged round bottom flask was added 1,2,3,4,5-pentamethylcyclopentadiene (0.6 mL, 3.83 mmol, 1 equiv), tetrabutylammonium iodide (140 mg, 0.38 mmol, 0.1 equiv), dry THF (8 mL), and a stir bar. The solution was cooled to 0° C. and n-butyllithium (2.33 M, 4.6 mmol, 1.2 equiv) was added dropwise. A white precipitate immediately began to form. The suspension was stirred for 45 min at 0° C., then paraformaldehyde from the previously refluxed solution (230 mg, 7.66 mmol, 2.0 equiv) was added and stirred for 18 h, letting the ice bath expire. The solvent was then removed solvent under reduced pressure and the solids were redissolved/resuspended in diethyl ether. This mixture was washed sequentially with 1.0 M HCl, sat. $NaHCO_3$ aq, and $H_2O$. The organic solution was dried over $Na_2SO_4$ and the solvent was removed under reduced pressure. The crude mixture was then purified by flash column chromatography to give a light yellow oil in 56% yield. $^1$H NMR (300 MHz, CDCl$_3$) δ 3.50 (s, 2H), 1.77 (d, J=18.8 Hz, 12H), 0.87 (s, 3H). $^{13}$C NMR (126 MHz, CDCl$_3$) δ 138.03 (s), 136.22 (s), 65.27 (s), 58.40 (s), 16.80 (s), 11.28 (s), 9.70 (s).

Synthesis of 32 (Scheme 15)

A flame-dried round bottom flask under nitrogen was charged with S5 (679 mg, 4.08 mmol, 1 equiv), dry $CH_2Cl_2$ (18 mL), and a stir bar. The solution was cooled to 0° C. and Et$_3$N (0.63 mL, 4.49 mmol, 1.1 equiv) was added. A solution of 2-chloropropionyl chloride (0.44 mL, 4.49 mmol, 1.1 equiv) in dry $CH_2Cl_2$ (6 mL) was made prepared under a $N_2$ atmosphere and added dropwise to the solution containing S5. The reaction mixture was stirred for 18 h, letting the ice bath expire. The reaction solvent was then removed under reduced pressure and the solids were taken up in diethyl ether. This mixture was washed sequentially with saturated aqueous $NaHCO_3$, and $H_2O$. The organic solution was dried over $Na_2SO_4$ and the solvent was removed under reduced pressure to give a yellow/brown oil. The product was isolated by flash column chromatography to obtain a transparent yellow oil in 71% yield. $^1$H NMR (300 MHz, CDCl$_3$) δ 4.31 (m, J=13.9, 7.0 Hz, 1H), 4.05 (q, J=10.7 Hz, 2H), 1.75 (s, 12H), 1.59 (d, J=7.0 Hz, 3H), 0.96 (s, 3H). $^{13}$C NMR (75 MHz, CDCl$_3$) δ 170.00 (s), 138.35 (s), 135.41 (s), 68.89 (s), 55.70 (s), 52.90 (s), 21.72 (s), 16.81 (s), 11.18 (s), 10.30 (s).

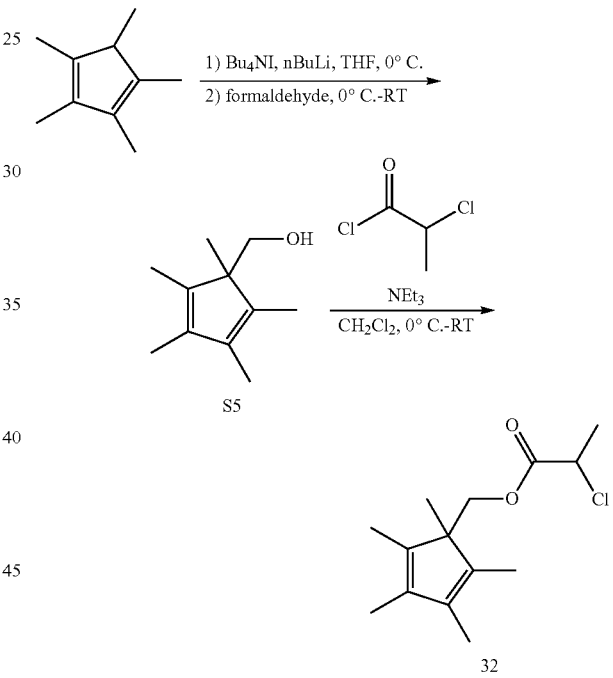

Scheme 15

Synthesis of 33 (Scheme 16)

Freshly distilled DMA (11.2 mL, 109 mmol, 350 equiv to initiator), CuCl (92 mg, 0.93 mmol, 3.0 equiv), and dry toluene (10 mL) were added to a Schlenk tube in a glove box. The reaction solution underwent three freeze-pump-thaw cycles, after which Me$_6$TREN (0.25 mL, 0.93 mmol, 3.0 equiv) was added and stirred for 30 min. Lastly, 32 (82 mg, 0.31 mmol, 1.0 equiv) was added and the polymerization was stirred for 5 h at RT. The reaction solution was diluted with THF and put through an alumina plug. The polymer solution was concentrated under vacuum and redissolved in approximately 4 mL of $CH_2Cl_2$. A saturated EDTA aq. solution (1 mL) was added and the layers were stirred vigorously so that remaining copper would be absorbed into the aqueous layer. Sodium sulfate was then added to dry the solution. The remaining solids were removed by filtration and the solvent was removed from the solution under reduced pressure. The resulting oily polymer residue was then redissolved in a minimal volume of pyridine and precipitated into ether (approximately 10 times the volume of the polymer solution). The precipitate was collected on a sintered-glass Büchner funnel and dried under vacuum. An off-white powder was recovered in 10% yield (1.08 g). $M_w$=27.8 kDa, PDI=1.07.

Synthesis of 34 (Scheme 16)

A flame-dried round-bottom flask was charged with SIP 2 (688 mg, 0.43 mmol, 1 equiv) and dry DMSO (10 mL). Once the SIP fully dissolved, 33 (1.08 g, 0.043 mmol, 0.1 equiv) and THF (10 mL) were added followed by CuCl (34 mg, 0.34 mmol, 0.8 equiv) and pyridine (7 µL, 0.086 mmol, 0.2 equiv). The reaction solution was stirred (open to air) for 24 h at RT. The solution was then precipitated into $CH_2Cl_2$ and filtered through a Celite/alumina plug in a sintered-glass Büchner funnel. The $CH_2Cl_2$ was then removed under reduced pressure and the remaining DMSO/polymer solution was added into diethyl ether. The polymer oiled out on bottom of flask. After decanting away the ether solution, the polymer dissolved in a minimal volume of $CH_2Cl_2$ and precipitated into ether. The precipitate was collected on in a sintered-glass Büchner funnel then dried under vacuum. A slightly off-white powder was recovered in 37% yield (402 mg). $M_w$=32.1 kDa, PDI=1.04.

Scheme 16

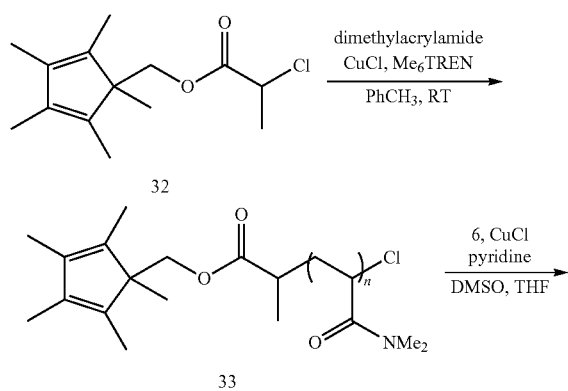

-continued

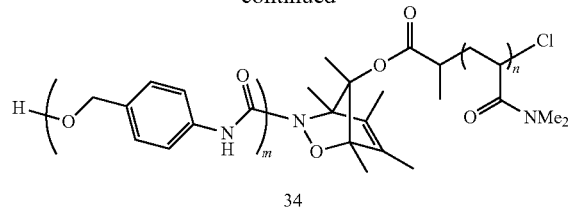

General Method for Monitoring the Thermally Triggered Depolymerization of 34 (Scheme 17. Data Shown in FIG. 5 and Table 2).

Diblock 34 (20 mg) was dissolved in anhydrous DMSO-$d_6$ (0.9 mL) and transferred to a screw cap NMR tube. $D_2O$ (0.1 mL) and 1,4-dicyanobenzene (1 mg) were then added. A time-zero NMR spectrum was collected. The NMR tube was then immersed in a pre-heated oil bath set to the desired temperature and the thermal decomposition progress was monitored at various time points by NMR spectroscopy until decomposition was complete.

Scheme 17

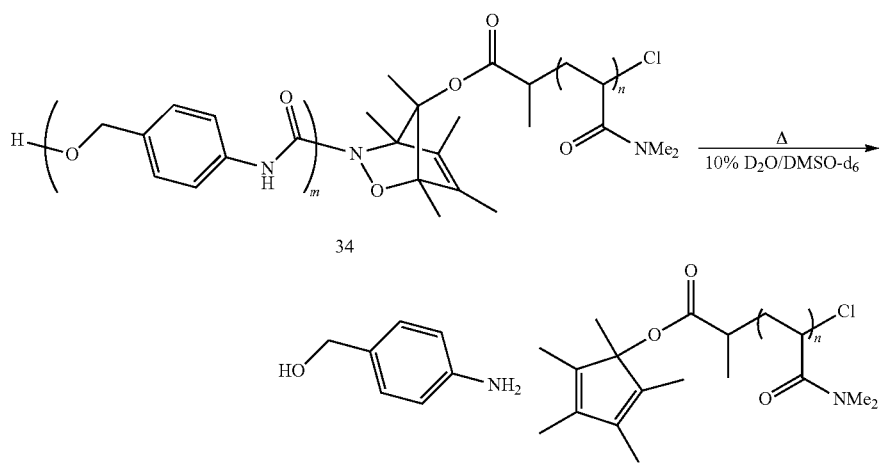

Synthesis of SIP 35 (Scheme 18)

A flame-dried round-bottom flask under $N_2$ was charged with the self-immolative monomer 1 (200 mg, 0.82 mmol, 1.0 equiv) and a stir bar. Dry DMSO (0.4 mL, 5 at 2.0 M) and dry $Et_3N$ (0.11 mL, 0.82 mmol, 1.0 equiv) were then added. The solution was heated at 60° C. for 3 h. To the reaction mixture was then added methoxymethylamine (0.51 mmol, 5.0 equiv relative to end group) from a 1.0 M stock solution prepared in dry DMSO. The resulting mixture was stirred for 17 h at 50° C. The reaction mixture was then poured into MeOH (approximately 10 times the volume of DMSO) and cooled in a refrigerator causing precipitation of the polymer. The precipitate was collected on a sintered-glass Büchner funnel, rinsed with $CH_2Cl_2$, and dried under vacuum. The product was obtained in 84% yield. Technical note: the methoxymethylamine solution was prepared by combining methoxymethylamine hydrochloride (10 mmol) with anhydrous $K_2CO_3$ (20 mmol) in dry DMSO (10 mL). The mixture was stored at RT for 12 h prior to use.

Scheme 18

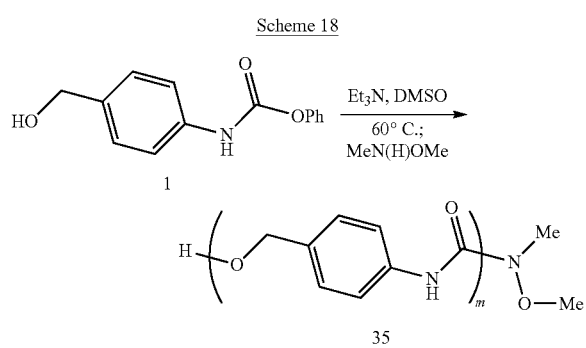

Diene Transfer with Diblock 34 (Scheme 19)

Diblock 34 (20 mg, 1.0 equiv) was dissolved in anhydrous DMSO-$d_6$ (0.88 mL) and transferred to a screw cap NMR tube. $D_2O$ (0.1 mL), 1,3-cyclohexadiene (0.019 mL, 300 equiv) and 1,4-dicyanobenzene (1 mg) were then added. A time-zero NMR spectrum was collected. The NMR tube was then immersed in a pre-heated oil bath set 60° C. and the thermal decomposition progress was monitored by $^1$H NMR spectroscopy. The rate of depolymerization was reduced in the presence of 1,3-cyclohexadiene, consistent with trapping of the intermediate carbamoylnitroso species to form a thermally more stable oxazine.

Scheme 19

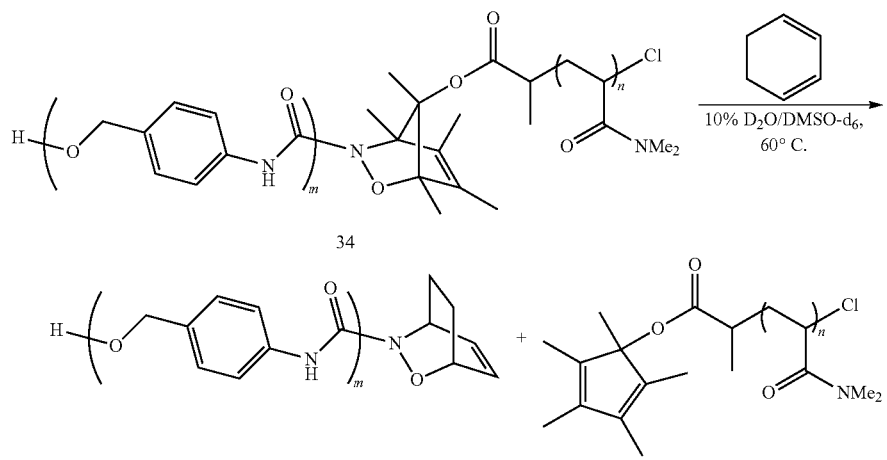

While illustrative embodiments have been illustrated and described, it will be appreciated that various changes can be made therein without departing from the spirit and scope of the invention.

What is claimed is:

1. A polymer comprising:
   (a) a self-immolative polymer segment comprising a head end, a tail end, and a plurality of repeating units; and
   (b) a trigger moiety comprising a cycloaddition adduct, wherein the cycloaddition adduct is covalently coupled to the head end of the self-immolative polymer segment,
   wherein the trigger moiety is configured to undergo a retro-cycloaddition reaction at a triggering temperature to cause the self-immolative polymer segment to decompose by releasing repeating units in a sequential head-to-tail direction, and wherein the retro-cycloaddition reaction provides a diene and a carbamoylnitroso moiety.

2. The polymer of claim 1, wherein the cycloaddition adduct is a [4+2] cycloaddition adduct.

3. The polymer of claim 1, wherein the trigger moiety comprises an adduct of a diene and a dienophile.

4. The polymer of claim 3, wherein the diene is selected from the group consisting of anthracene, cyclopentadiene, 1,2,3,4,5-pentamethylcyclopentadiene, 1-hydroxymethyl-1,2,3,4,5-pentamethylcyclopentadiene, 1,3-cyclohexadiene, 1,3-butadiene, safranal, 1-hydroxymethyl-2,6,6-trimethyl-1,3-cyclohexadiene, cycloheptatriene, tropolone, butyltropolone, hinokitiol, butylhinokitiol, eucarvone, eucarveol, purpurogallin, trimethylpurpurogallin, 7-dehydrocholesterol, 3,5-cycloheptadienol, and substituted derivatives thereof.

5. The polymer of claim 3, wherein the diene is substituted.

6. The polymer of claim 3, wherein the dienophile comprises a maleimide moiety, acetylene moiety, a carbamoylnitroso moiety, an alkene moiety, or an azo moiety.

7. The polymer of claim 1, wherein prior to incorporation into the self-immolative polymer segment, the repeating unit comprises an optionally substituted carbamate moiety, optionally substituted carbonate moiety, optionally substituted benzylic ether moiety, or an optionally substituted acetal moiety.

8. The polymer of claim 1, further comprising a covalently bound therapeutic agent.

9. The polymer of claim 8, wherein the therapeutic agent is covalently bound to at least one of the repeating units.

10. The polymer of claim 9, wherein when the repeating unit to which the therapeutic agent is covalently bound to release, the therapeutic agent releases simultaneously with or subsequent to the release of the repeating unit.

11. The polymer of claim 1, further comprising a water-soluble polymer segment covalently coupled to the self-immolative polymer segment.

12. The polymer of claim 11, wherein the water-soluble polymer segment comprises poly(ethylene glycol), poly(dimethylacrylamide), poly(vinylpyrrolidone), poly(vinyl alcohol), poly (N-(2-Hydroxypropyl) methacrylamide), poly (divinylether-maleic anhydride), poly(2-alkyl-2-oxazolines), xantham gum, pectin, dextran, or any combination thereof.

13. The polymer of claim 11, wherein the polymer is water soluble.

14. The polymer of claim 1, wherein the triggering temperature is from about 37° C. to about 120° C.

15. The polymer of claim 1, wherein the triggering temperature is at about a physiological temperature.

16. A method for releasing one or more repeating units from a polymer, comprising:
  subjecting a polymer according to claim 1 to a temperature sufficient to trigger retro-cycloaddition of the cycloaddition adduct to release the self-immolative polymer segment, wherein the self-immolative polymer segment then decomposes to sequentially release repeating units in a head-to-tail direction.

17. A method for making a patterned structure, comprising:
  (a) applying a polymer of claim 1 to a substrate; and
  (b) heating the substrate at predetermined locations to a temperature sufficient to effect depolymerization of the polymer to provide a patterned structure.

18. The method of claim 17, wherein the polymer is applied at the predetermined locations.

19. The method of claim 17, further comprising (c) applying one or more additional materials to the substrate before step (b).

20. A polymer comprising:
  (a) a self-immolative polymer segment comprising a head end, a tail end, and a plurality of repeating units; and
  (b) a trigger moiety comprising a cycloaddition adduct, wherein the cycloaddition adduct is covalently coupled to the head end of the self-immolative polymer segment,
  wherein the repeating unit is selected from the group consisting of:

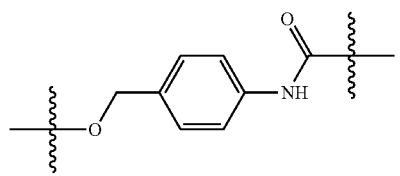

,

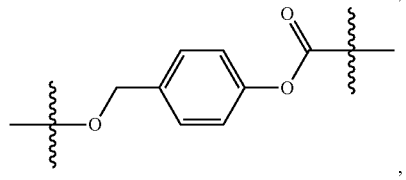

,

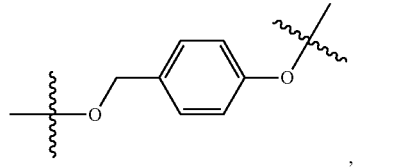

,

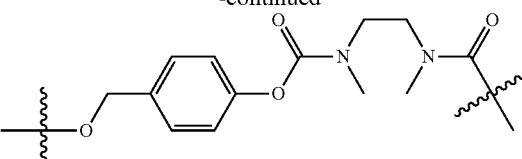

,

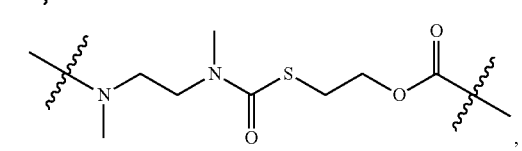

,

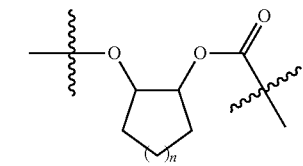

,

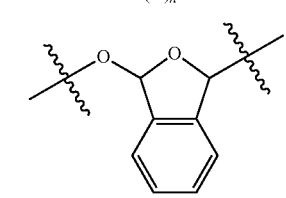

, and substituted derivatives thereof.

21. The polymer of claim 20, further comprising a covalently bound therapeutic agent.

22. The polymer of claim 21, wherein the therapeutic agent is covalently bound to at least one of the repeating units.

23. A polymer comprising:
  (a) a self-immolative polymer segment comprising a head end, a tail end, and a plurality of repeating units; and
  (b) a trigger moiety comprising a cycloaddition adduct, wherein the cycloaddition adduct is covalently coupled to the head end of the self-immolative polymer segment,
  wherein the trigger moiety is configured to undergo a retro-cycloaddition reaction at a triggering temperature to cause the self-immolative polymer segment to decompose by releasing repeating units in a sequential head-to-tail direction, and the triggering temperature is at about a physiological temperature.

24. The polymer of claim 23, further comprising a covalently bound therapeutic agent.

25. The polymer of claim 24, wherein the therapeutic agent is covalently bound to at least one of the repeating units.

* * * * *